(12) United States Patent
Fortson

(10) Patent No.: US 10,426,449 B2
(45) Date of Patent: Oct. 1, 2019

(54) ARTICULATING SUTURING DEVICE WITH IMPROVED ACTUATION AND ALIGNMENT MECHANISMS

(71) Applicant: Abbott Cardiovascular Systems, Inc., Santa Clara, CA (US)

(72) Inventor: Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 206 days.

(21) Appl. No.: 15/434,907

(22) Filed: Feb. 16, 2017

(65) Prior Publication Data

US 2018/0228478 A1  Aug. 16, 2018

(51) Int. Cl.
| | |
|---|---|
| *A61B 17/12* | (2006.01) |
| *A61B 17/00* | (2006.01) |
| *A61B 17/04* | (2006.01) |
| *A61B 90/00* | (2016.01) |

(52) U.S. Cl.
CPC ...... *A61B 17/0057* (2013.01); *A61B 2017/00367* (2013.01); *A61B 2017/00455* (2013.01); *A61B 2017/00623* (2013.01); *A61B 2017/00663* (2013.01); *A61B 2017/00672* (2013.01); *A61B 2017/0472* (2013.01); *A61B 2090/0811* (2016.02)

(58) Field of Classification Search
CPC ......... A61B 17/00; A61B 17/04; A61B 17/12; A61B 17/0057; A61B 17/0482; A61B 17/0483; A61B 17/0469; A61B 2017/0472; A61B 2017/00663
See application file for complete search history.

(56) References Cited

U.S. PATENT DOCUMENTS

| | | | |
|---|---|---|---|
| 312,408 | A | 2/1885 | Wackerhagen |
| 597,165 | A | 1/1898 | Hall |
| 659,422 | A | 10/1900 | Shidler |
| 989,231 | A | 4/1911 | Davis |
| 1,574,362 | A | 9/1922 | Callahan |
| 1,625,602 | A | 4/1927 | Gould et al. |
| 1,940,351 | A | 3/1933 | Howard |
| 2,012,776 | A | 8/1935 | Roeder |
| 2,131,321 | A | 10/1937 | Hart |
| 2,127,903 | A | 8/1938 | Bowen |
| 2,371,978 | A | 3/1945 | Perham |
| 2,397,823 | A | 4/1946 | Walter |
| RE22,857 | E | 3/1947 | Ogburn |
| 2,595,086 | A | 11/1948 | Larzelere |
| 2,588,589 | A | 3/1952 | Tauber |

(Continued)

FOREIGN PATENT DOCUMENTS

| | | |
|---|---|---|
| DE | 912619 | 5/1954 |
| DE | 4210724 | 7/1993 |

(Continued)

OTHER PUBLICATIONS

US 5,820,544 A, 06/1974, Semm (withdrawn)

(Continued)

*Primary Examiner* — Vi X Nguyen
(74) *Attorney, Agent, or Firm* — Workman Nydegger; Randy Shen

(57) ABSTRACT

A vessel closure device that includes improved activation and alignment mechanisms that result in greater control and ease of use for the user.

15 Claims, 15 Drawing Sheets

(56) References Cited

U.S. PATENT DOCUMENTS

| | | |
|---|---|---|
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,580,566 A | 4/1986 | Hsu |
| 4,586,614 A | 5/1986 | Ger |
| 4,587,969 A | 5/1986 | Gillis |
| 4,596,559 A | 6/1986 | Fleishhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,823,794 A | 4/1989 | Pierce |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yo on |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |

(56) References Cited

U.S. PATENT DOCUMENTS

| | | |
|---|---|---|
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Delia Badia et al. |
| 5,397,326 A | 3/1995 | Mangum |
| 5,403,329 A | 4/1995 | Hinchcliffe |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,578,044 A | 11/1996 | Gordon et al. |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,649,959 A | 7/1997 | Hannam et al. |
| 5,662,664 A | 9/1997 | Gordon et al. |
| 5,669,917 A | 9/1997 | Sauer et al. |
| 5,676,689 A | 10/1997 | Kensey et al. |
| 5,700,273 A | 12/1997 | Buelna et al. |
| 5,707,379 A | 1/1998 | Fleenor et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,810,884 A | 9/1998 | Kim |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |

(56) References Cited

U.S. PATENT DOCUMENTS

| | | |
|---|---|---|
| 5,830,125 A | 11/1998 | Scribner et al. |
| 5,836,315 A | 11/1998 | Benderev et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,895,404 A | 4/1999 | Ruiz |
| 5,897,487 A | 4/1999 | Ouchi |
| 5,897,564 A | 4/1999 | Schulze et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,539 A | 11/1999 | Kontos |
| 5,997,555 A | 12/1999 | Kontos |
| 6,001,109 A | 12/1999 | Kontos |
| 6,022,372 A | 2/2000 | Kontos |
| 6,024,747 A | 2/2000 | Kontos |
| 6,036,699 A * | 3/2000 | Andreas ............ A61B 17/0057 606/139 |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,059,800 A | 5/2000 | Hart et al. |
| 6,068,603 A | 5/2000 | Suzuki |
| 6,077,276 A | 6/2000 | Kontos |
| 6,077,279 A | 6/2000 | Kontos |
| 6,102,920 A | 8/2000 | Sullivan et al. |
| 6,117,144 A | 9/2000 | Nobles et al. |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson |
| 6,245,079 B1 | 6/2001 | Nobles et al. |
| 6,248,124 B1 | 6/2001 | Pedros et al. |
| 6,296,657 B1 | 10/2001 | Brucker |
| 6,302,870 B1 | 10/2001 | Jacobsen et al. |
| 6,346,111 B1 | 2/2002 | Gordon et al. |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,511,489 B2 | 1/2003 | Field et al. |
| 6,517,553 B2 | 2/2003 | Klein et al. |
| 6,533,812 B2 | 3/2003 | Swanson et al. |
| 6,551,329 B1 | 4/2003 | Kortenbach et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,749,621 B2 | 6/2004 | Pantages et al. |
| 6,749,622 B2 | 6/2004 | McGuckin, Jr. et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,936,054 B2 | 8/2005 | Chu |
| 6,939,357 B2 | 9/2005 | Navarro et al. |
| 6,955,643 B2 | 10/2005 | Gellman et al. |
| 6,964,668 B2 | 11/2005 | Modesitt et al. |
| 6,969,371 B2 | 11/2005 | Palasis et al. |
| 6,969,397 B2 | 11/2005 | Ginn |
| 6,997,932 B2 | 2/2006 | Dreyfuss et al. |
| 7,001,400 B1 | 2/2006 | Modesitt et al. |
| 7,029,480 B2 | 4/2006 | Klein et al. |
| 7,029,481 B1 | 4/2006 | Burdulis, Jr. et al. |
| 7,033,370 B2 | 4/2006 | Gordon et al. |
| 7,048,747 B2 | 5/2006 | Arcia et al. |
| 7,063,710 B2 * | 6/2006 | Takamoto .......... A61B 17/0469 606/139 |
| 7,066,077 B2 | 6/2006 | Schnapp et al. |
| 7,083,635 B2 | 8/2006 | Ginn |
| 7,108,710 B2 | 9/2006 | Anderson |
| 7,112,225 B2 | 9/2006 | Ginn |
| 7,131,980 B1 | 11/2006 | Field et al. |
| 7,160,309 B2 | 1/2007 | Voss |
| 7,179,266 B2 | 2/2007 | Kontos |
| 7,229,458 B2 | 6/2007 | Boecker et al. |
| 7,235,087 B2 | 6/2007 | Modesitt et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,753,923 B2 | 7/2010 | St. Goar et al. |
| 7,833,235 B2 | 11/2010 | Chu |
| 7,837,696 B2 | 11/2010 | Modesitt et al. |
| 7,842,047 B2 | 11/2010 | Modesitt et al. |
| 7,842,048 B2 | 11/2010 | Ma |
| 7,842,049 B2 | 11/2010 | Voss |
| 7,846,170 B2 | 12/2010 | Modesitt et al. |
| 7,850,701 B2 | 12/2010 | Modesitt |
| 7,883,517 B2 | 2/2011 | Pantages et al. |
| 7,935,128 B2 | 5/2011 | Rioux et al. |
| 7,967,832 B2 | 6/2011 | Chu |
| 8,038,688 B2 | 10/2011 | Modesitt et al. |

(56) References Cited

U.S. PATENT DOCUMENTS

| | | |
|---|---|---|
| 8,048,092 B2 | 11/2011 | Modesitt et al. |
| 8,057,491 B2 | 11/2011 | Modesitt et al. |
| 8,083,754 B2 | 12/2011 | Pantages et al. |
| 8,123,762 B2 | 2/2012 | Chu et al. |
| 8,137,364 B2 | 3/2012 | Zung et al. |
| 8,172,860 B2 | 5/2012 | Zung et al. |
| 8,202,281 B2 | 6/2012 | Voss |
| 8,211,122 B2 | 7/2012 | McIntosh |
| 8,252,008 B2 | 8/2012 | Ma |
| 8,257,368 B2 | 9/2012 | McIntosh |
| 8,267,947 B2 | 9/2012 | Pantages et al. |
| 8,313,498 B2 | 11/2012 | Pantages et al. |
| 8,323,298 B2 | 12/2012 | Modesitt et al. |
| 8,361,088 B2 | 1/2013 | McIntosh |
| 8,419,753 B2 | 4/2013 | Stafford |
| 8,430,893 B2 | 4/2013 | Ma |
| 8,512,375 B2 | 8/2013 | Torrie et al. |
| 8,574,244 B2 | 11/2013 | Reynolds |
| 8,597,309 B2 | 12/2013 | Stafford |
| 8,663,248 B2 | 3/2014 | Zung et al. |
| 8,663,252 B2 | 3/2014 | Fortson |
| 8,858,573 B2 | 10/2014 | Fortson et al. |
| 8,864,778 B2 | 10/2014 | Fortson et al. |
| 8,998,932 B2 | 4/2015 | Voss |
| 9,155,535 B2 | 10/2015 | McIntosh |
| 9,241,707 B2 | 1/2016 | Roorda et al. |
| 9,282,960 B2 | 3/2016 | Ma |
| 9,301,747 B2 | 4/2016 | Zung et al. |
| 9,370,353 B2 | 6/2016 | Fortson et al. |
| 9,375,211 B2 | 6/2016 | Stafford |
| 9,592,038 B2 | 3/2017 | Pantages et al. |
| 9,820,730 B2 | 11/2017 | Chu |
| 2001/0046518 A1 | 11/2001 | Sawhney |
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0107531 A1 | 8/2002 | Schreck et al. |
| 2002/0177876 A1 | 11/2002 | Roby et al. |
| 2003/0093093 A1 | 5/2003 | Modesitt et al. |
| 2003/0171764 A1 | 9/2003 | Debbas |
| 2003/0195529 A1 | 10/2003 | Takamoto et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0069397 A1 | 3/2006 | Nobles et al. |
| 2006/0100664 A1 | 5/2006 | Pai et al. |
| 2006/0167477 A1 | 7/2006 | Arcia et al. |
| 2006/0173469 A1 | 8/2006 | Klein |
| 2006/0253037 A1 | 11/2006 | Ginn et al. |
| 2006/0253072 A1 | 11/2006 | Pai et al. |
| 2007/0005079 A1 | 1/2007 | Zarbatany et al. |
| 2007/0032801 A1 | 2/2007 | Pantages et al. |
| 2007/0060950 A1 | 3/2007 | Khosravi et al. |
| 2007/0123817 A1 | 5/2007 | Khosravi et al. |
| 2007/0282354 A1 | 12/2007 | McIntosh |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0287967 A1 | 11/2008 | Andreas et al. |
| 2011/0071567 A1 | 3/2011 | Modesitt et al. |
| 2011/0190793 A1 | 8/2011 | Nobles et al. |
| 2011/0288563 A1 | 11/2011 | Gianotti et al. |
| 2012/0016383 A1 | 1/2012 | Sauer et al. |
| 2012/0150201 A1 | 6/2012 | Pantages et al. |
| 2012/0283749 A1 | 11/2012 | Sauer |
| 2013/0012962 A1 | 1/2013 | Stone |
| 2014/0236189 A1 | 8/2014 | Melsheimer et al. |
| 2015/0025551 A1 | 1/2015 | Fortson et al. |
| 2015/0119906 A1 | 4/2015 | Bagaoisan et al. |
| 2015/0273186 A1 | 10/2015 | Voss |
| 2016/0135803 A1 | 5/2016 | McIntosh |
| 2016/0135805 A1 | 5/2016 | Roorda et al. |
| 2016/0192914 A1 | 7/2016 | Ma |
| 2016/0287229 A1 | 10/2016 | Zung et al. |
| 2016/0367234 A1 | 12/2016 | Fortson et al. |
| 2016/0367241 A1 | 12/2016 | Stafford |
| 2018/0338759 A1 | 11/2018 | Roorda et al. |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |

(56) References Cited

FOREIGN PATENT DOCUMENTS

| | | |
|---|---|---|
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/036021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 05/000126 | 1/2005 |
| WO | WO 05/023119 | 3/2005 |
| WO | WO 05/025430 | 3/2005 |
| WO | WO 05/030060 | 4/2005 |
| WO | WO 05/041782 | 5/2005 |
| WO | WO 05/063129 | 7/2005 |
| WO | WO 05/065549 | 7/2005 |
| WO | WO 05/092204 | 10/2005 |
| WO | WO 05/112782 | 12/2005 |
| WO | WO 06/026116 | 3/2006 |
| WO | WO 06/052611 | 5/2006 |
| WO | WO 06/052612 | 5/2006 |
| WO | WO 06/078578 | 7/2006 |
| WO | WO 06/115901 | 11/2006 |
| WO | WO 06/115904 | 11/2006 |
| WO | WO 06/118877 | 11/2006 |
| WO | WO 07/019016 | 2/2007 |
| WO | WO 07/081836 | 7/2007 |

OTHER PUBLICATIONS

U.S. Appl. No. 14/511,730, Oct. 13, 2017, Office Action.
U.S. Appl. No. 14/511,730, Jun. 11, 2018, Office Action.
U.S. Appl. No. 14/511,730, Oct. 31, 2018, Interview Summary.
U.S. Appl. No. 14/674,756, Jul. 6, 2017, Office Action.
U.S. Appl. No. 14/674,756, Sep. 18, 2017, Notice of Allowance.
U.S. Appl. No. 14/880,894, Oct. 31, 2017, Office Action.
U.S. Appl. No. 14/880,894, Apr. 2, 2018, Office Action.
U.S. Appl. No. 14/880,894, Aug. 6, 2018, Office Action.
U.S. Appl. No. 14/880,894, Nov. 21, 2018, Notice of Allowance.
U.S. Appl. No. 15/005,880, Nov. 13, 2017, Office Action.
U.S. Appl. No. 15/005,880, Apr. 10, 2018, Office Action.
U.S. Appl. No. 15/005,880, Jun. 20, 2018, Interview Summary.
U.S. Appl. No. 15/005,880, Jul. 13, 2018, Notice of Allowance.
U.S. Appl. No. 15/069,515, Mar. 20, 2018, Notice of Allowance.
U.S. Appl. No. 15/090,150, Dec. 12, 2018, Office Action.
U.S. Appl. No. 15/186,730, Sep. 5, 2018, Office Action.
U.S. Appl. No. 15/192,481, Jul. 20, 2018, Office Action.
U.S. Appl. No. 15/192,481, Oct. 31, 2018, Interview Summary.
U.S. Appl. No. 15/192,481, Jan. 11, 2019, Office Action.
U.S. Appl. No. 60/540,811, Jan. 30, 2004, McIntosh.
U.S. Appl. No. 60/946,063, Jun. 25, 2007, Reynolds.
U.S. Appl. No. 90/006,469, Nov. 29, 2002, Modesitt et al.
Cardiac Catheterization and Angiography, 3rd Ed., Lea & Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Definition of "pair", Dictionary.com, accessed on May 5, 2014.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintechnik GmbH, Product Brochure entitled "REMA," Apr. 2001, 7 pages.
Serruys, PW et al., A Comparision of Balloon-Expandable-Stent Implantation With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, May 12, 1993, Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.
U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/262,402, Mar. 29, 2000, Office Action.
U.S. Appl. No. 09/262,402, May 30, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/152,272, Jan. 24, 2005, Office Action.
U.S. Appl. No. 10/152,272, May 13, 2005, Notice of Allowance.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.

(56) References Cited

OTHER PUBLICATIONS

U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/660,288, Mar. 29, 2011, Office Action.
U.S. Appl. No. 10/660,288, Sep. 30, 2011, Notice of Allowance.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 10/948,445, Jul. 11, 2007, Office Action.
U.S. Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,496, Apr. 28, 2011, Office Action.
U.S. Appl. No. 11/199,496, Aug. 18, 2011, Notice of Allowance.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273,107, Oct. 28, 2009, Office Action.
U.S. Appl. No. 11/273,107, Jun. 2, 2010, Office Action.
U.S. Appl. No. 11/273,107, Oct. 27, 2010, Office Action.
U.S. Appl. No. 11/273,107, Jun. 2, 2011, Notice of Allowance.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/552,593, Jul. 22, 2010, Notice of Allowance.
U.S. Appl. No. 11/688,722, Mar. 10, 2010, Office Action.
U.S. Appl. No. 11/688,722, Jul. 29, 2010, Notice of Allowance.
U.S. Appl. No. 11/891,358, Apr. 26, 2010, Office Action.
U.S. Appl. No. 11/891,358, Oct. 19, 2010, Office Action.
U.S. Appl. No. 11/891,358, Aug. 31, 2011, Office Action.
U.S. Appl. No. 11/891,358, Nov. 18, 2011, Notice of Allowance.
U.S. Appl. No. 11/891,358, Apr. 10, 2012, Notice of Allowance.
U.S. Appl. No. 11/891,513, Apr. 9, 2010, Office Action.
U.S. Appl. No. 11/891,513, Sep. 28, 2010, Office Action.
U.S. Appl. No. 11/891,513, Aug. 31, 2011, Office Action.
U.S. Appl. No. 11/891,513, Nov. 1, 2011, Notice of Allowance.
U.S. Appl. No. 11/891,513, May 8, 2012, Notice of Allowance.
U.S. Appl. No. 11/960,593, Sep. 14, 2010, Office Action.
U.S. Appl. No. 11/960,593, Nov. 3, 2010, Office Action.
U.S. Appl. No. 11/960,593, Apr. 28, 2011, Office Action.
U.S. Appl. No. 11/960,593, Jul. 1, 2013, Notice of Allowance.
U.S. Appl. No. 11/997,379, Jul. 13, 2011, Office Action.
U.S. Appl. No. 11/997,379, Feb. 28, 2012, Office Action.
U.S. Appl. No. 11/997,379, May 11, 2012, Notice of Allowance.
U.S. Appl. No. 12/182,836, Oct. 5, 2010, Office Action.
U.S. Appl. No. 12/182,836, Jun. 23, 2011, Office Action.
U.S. Appl. No. 12/182,836, May 17, 2013, Office Action.
U.S. Appl. No. 12/247,012, Oct. 13, 2011, Office Action.
U.S. Appl. No. 12/247,012, Mar. 16, 2012, Office Action.
U.S. Appl. No. 12/247,012, Aug. 13, 2012, Notice of Allowance.
U.S. Appl. No. 12/257,127, Aug. 30, 2010, Office Action.
U.S. Appl. No. 12/257,127, Dec. 22, 2010, Office Action.
U.S. Appl. No. 12/257,127, Jul. 6, 2011, Office Action.
U.S. Appl. No. 12/257,127, Jan. 12, 2012, Office Action.
U.S. Appl. No. 12/257,127, Sep. 20, 2012, Notice of Allowance.
U.S. Appl. No. 12/334,077, Oct. 27, 2010, Office Action.
U.S. Appl. No. 12/334,077, Jul. 21, 2011, Office Action.
U.S. Appl. No. 12/334,077, Jan. 16, 2013, Office Action.
U.S. Appl. No. 12/334,077, Oct. 11, 2013, Notice of Allowance.
U.S. Appl. No. 12/334,085, Dec. 23, 2010, Office Action.
U.S. Appl. No. 12/334,085, Aug. 4, 2011, Office Action.
U.S. Appl. No. 12/334,085, Jan. 9, 2012, Notice of Allowance.
U.S. Appl. No. 12/873,728, Sep. 11, 2012, Office Action.
U.S. Appl. No. 12/873,728, May 3, 2013, Office Action.
U.S. Appl. No. 12/873,728, Aug. 23, 2013, Office Action.
U.S. Appl. No. 12/873,728, Nov. 4, 2013, Notice of Allowance.

(56) References Cited

OTHER PUBLICATIONS

U.S. Appl. No. 12/950,338, Jun. 15, 2011, Office Action.
U.S. Appl. No. 12/950,338, Nov. 1, 2011, Notice of Allowance.
U.S. Appl. No. 12/950,338, Aug. 8, 2012, Notice of Allowance.
U.S. Appl. No. 12/955,848, Jun. 30, 2011, Office Action.
U.S. Appl. No. 12/955,848, Nov. 15, 2011, Office Action.
U.S. Appl. No. 12/955,863, Jan. 6, 2012, Office Action.
U.S. Appl. No. 12/955,863, May 15, 2012, Notice of Allowance.
U.S. Appl. No. 12/955,869, Oct. 18, 2011, Office Action.
U.S. Appl. No. 12/955,869, Mar. 22, 2012, Notice of Allowance.
U.S. Appl. No. 12/961,239, Jul. 26, 2011, Notice of Allowance.
U.S. Appl. No. 12/966,961, Aug. 18, 2011, Notice of Allowance.
U.S. Appl. No. 13/022,050, Jul. 11, 2011, Office Action.
U.S. Appl. No. 13/022,050, Apr. 26, 2012, Office Action.
U.S. Appl. No. 13/022,050, Jul. 6, 2012, Notice of Allowance.
U.S. Appl. No. 13/333,411, Dec. 18, 2014, Office Action.
U.S. Appl. No. 13/333,411, Apr. 1, 2015, Office Action.
U.S. Appl. No. 13/333,411, Apr. 4, 2016, Office Action.
U.S. Appl. No. 13/443,659, Nov. 13, 2013, Office Action.
U.S. Appl. No. 13/443,659, Jun. 11, 2014, Notice of Allowance.
U.S. Appl. No. 13/455,053, Nov. 27, 2013, Office Action.
U.S. Appl. No. 13/455,053, Jun. 9, 2014, Notice of Allowance.
U.S. Appl. No. 13/485,388, May 21, 2015, Office Action.
U.S. Appl. No. 13/485,388, Oct. 7, 2015, Notice of Allowance.
U.S. Appl. No. 13/525,875, May 28, 2014, Office Action.
U.S. Appl. No. 13/525,875, Sep. 30, 2014, Office Action.
U.S. Appl. No. 13/525,875, Dec. 10, 2014, Notice of Allowance.
U.S. Appl. No. 13/593,154, Jan. 8, 2013, Notice of Allowance.
U.S. Appl. No. 13/615,523, Feb. 26, 2016, Office Action.
U.S. Appl. No. 13/615,523, Aug. 18, 2016, Office Action.
U.S. Appl. No. 13/615,523, Nov. 30, 2016, Notice of Allowance.
U.S. Appl. No. 13/615,530, Jan. 17, 2013, Office Action.
U.S. Appl. No. 13/615,530, Jun. 12, 2013, Notice of Allowance.
U.S. Appl. No. 13/752,095, Oct. 17, 2014, Office Action.
U.S. Appl. No. 13/752,095, Feb. 20, 2015, Office Action.
U.S. Appl. No. 13/752,095, Jun. 12, 2015, Notice of Allowance.
U.S. Appl. No. 13/791,858, Nov. 10, 2015, Office Action.
U.S. Appl. No. 13/791,858, Mar. 15, 2016, Notice of Allowance.
U.S. Appl. No. 13/870,628, Jul. 13, 2015, Office Action.
U.S. Appl. No. 13/870,628, Nov. 12, 2015, Notice of Allowance.
U.S. Appl. No. 14/094,352, Dec. 15, 2014, Office Action.
U.S. Appl. No. 14/094,352, Jul. 8, 2015, Office Action.
U.S. Appl. No. 14/094,352, Mar. 22, 2016, Notice of Allowance.
U.S. Appl. No. 14/195,308, Dec. 18, 2014, Office Action.
U.S. Appl. No. 14/195,308, Aug. 11, 2015, Office Action.
U.S. Appl. No. 14/195,308, Dec. 4, 2015, Notice of Allowance.
U.S. Appl. No. 14/511,730, Jan. 20, 2017, Office Action.
U.S. Appl. No. 14/674,756, Mar. 17, 2017, Office Action.
U.S. Appl. No. 90/006,469, Nov. 29, 2002, Request for Continued Examination.
U.S. Appl. No. 90/006,469, Sep. 10, 2004, Office Action.
U.S. Appl. No. 90/006,469, Sep. 27, 2005, Notice of Re-Issue.
U.S. Appl. No. 90/006,469, Jun. 27, 2006, Request for Continued Examination.

* cited by examiner

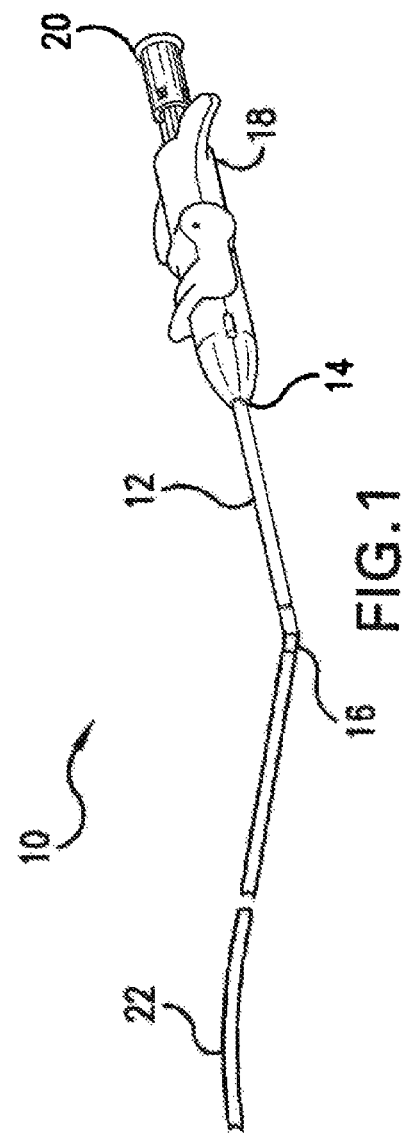

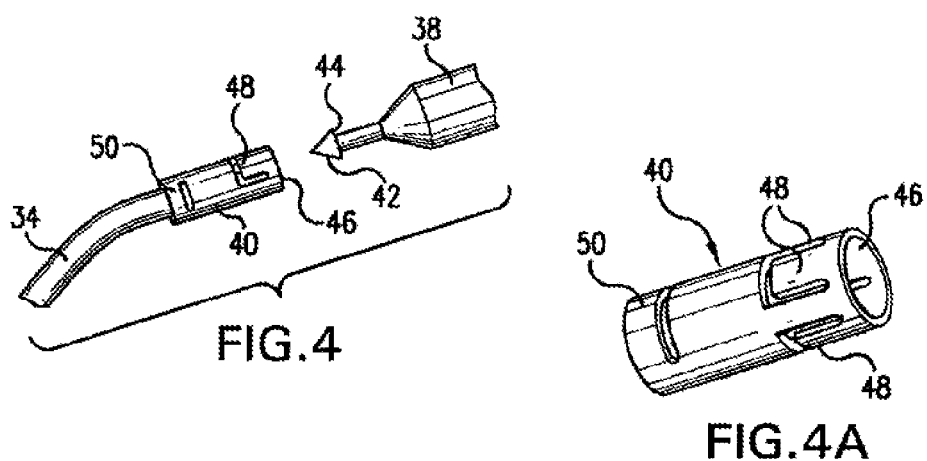
FIG.4
FIG.4A
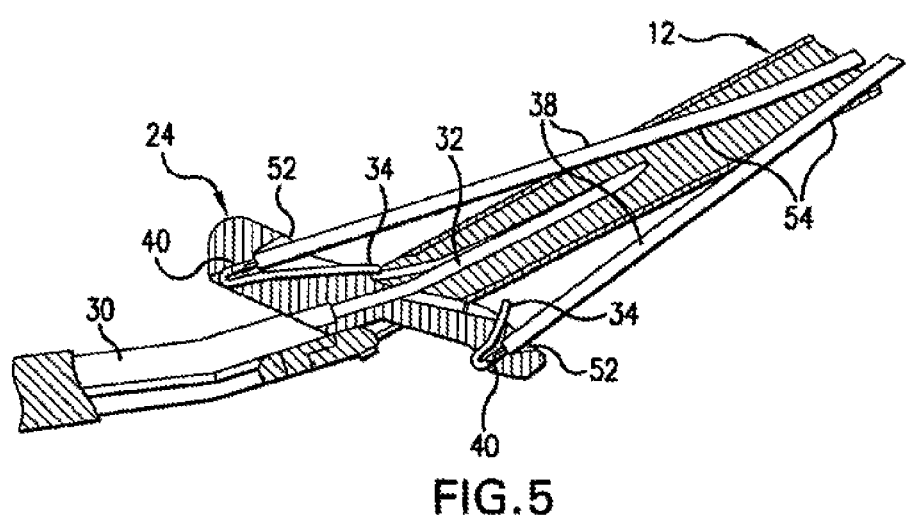
FIG.5

ARTICULATING SUTURING DEVICE WITH IMPROVED ACTUATION AND ALIGNMENT MECHANISMS

BACKGROUND OF THE INVENTION

The present invention relates generally to apparatus and methods for the suturing of body lumens. More particularly, the present invention relates to techniques for percutaneous closure of arterial and venous puncture sites, which are usually accessed through a tissue tract.

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," 3.sup.rd Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time renewed bleeding may occur, resulting in blood loss through the tract, hematoma and/or pseudo-aneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the arterial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 12, 1996, the full disclosures of which are incorporated herein by reference. A suture-applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device that is inserted into the tissue tract and/or the vessel itself, which may also allow closure of the vessel in a relatively short amount of time without imposing excessive injury to the tissue tract or vessel.

Another issue common among many of the prior art devices is the need for the user to reposition her or his hands one or more times during placement and operation of the closure device. Therefore, an actuation mechanism with improved ergonomic design that provides greater control and ease of use would also be desirable.

For the above reasons, it would be desirable to provide improved devices, systems, and methods for suturing vascular punctures. Such devices would have the capability of delivering a pre-tied knot to an incision site. It would be particularly beneficial if these improved devices provided some or all of the benefits while overcoming one or more of the disadvantages discussed above.

DESCRIPTION OF THE BACKGROUND ART

U.S. Pat. Nos. 5,700,273, 5,836,956, and 5,846,253 describe a wound closure apparatus and method in which needles are threaded with suture inside a blood vessel. U.S. Pat. No. 5,496,332 describes a wound closure apparatus and method for its use, while U.S. Pat. No. 5,364,408 describes an endoscopic suture system.

U.S. Pat. No. 5,374,275 describes a surgical suturing device and method of use, while U.S. Pat. No. 5,417,699 describes a device and method for the percutaneous suturing of a vascular puncture site. An instrument for closing trocar puncture wounds is described in U.S. Pat. No. 5,470,338, and a related device is described in U.S. Pat. No. 5,527,321, U.S. Pat. No. 5,507,757 also describes a method of closing puncture wounds.

SUMMARY OF THE INVENTION

The present invention provides improved devices, systems, and methods for suturing of body lumens. The device often allows the suturing of vascular puncture sites located at the distal end of a percutaneous tissue tract with greater ease, in less time, and with less patient trauma than known systems. These improvements are generally provided through the use of shafts having smaller cross-sections than prior suturing systems. In the exemplary embodiment, an elongate articulated foot near a distal end of a shaft is inserted through the penetration and actuated so that the foot extends along the lumenal axis. The foot carries suture attachment cuffs, and can be drawn proximally up against the endothelial surface of the blood vessel. Needles are advanced from the shaft, through the vessel wall beyond the penetration, and into engagement with the needle cuffs. The cross-section of the shaft within the tissue tract can be minimized by laterally deflecting the needles before they leave the shaft, while tapered depressions within the foot can help guide the advancing needles into engagement with the cuffs. The cuffs positively engage and capture or trap the needles so that the cuffs can be withdrawn proximally along the needle paths through the tissue tract to form a loop of suture across the puncture without having to thread the needles directly with the suture inside the blood vessel. The suture loop may be drawn distally from the shaft, proximally from within the blood vessel, or laterally down one of the needle paths, across the puncture, and out the opposing path. Regardless, the articulating foot may be realigned with the shaft and withdrawn proximally through the tissue tract in a small profile configuration. The use of an articulatable foot in combination with lateral deflection of the needles can avoid dilation of the tissue tract, as was often necessary using known puncture closure systems.

In a first aspect, the invention provides a method for suturing a puncture through a vessel wall of a blood vessel. The puncture is disposed within a tissue tract of a patient body, and the method comprises attaching a flexible filament to a first fitting. The first fitting is inserted through the tissue tract and positioned adjacent the vessel wall, and a needle path is formed by advancing a first needle through the vessel wall. The needle is coupled with the first fitting, and the first needle, the first fitting, and at least a portion of the filament are withdrawn through the vessel wall along the needle path.

First and second fittings will often be coupled to the flexible filament, and will generally be positioned so that the puncture is disposed therebetween. The flexible filament will often comprise a suture extending between the first and second fittings, with each fitting being drawn proximally by an associated needle to form the suture loop. Alternatively, at least one of the needles may include a detachable tip and may advance a suture distally along the needle path as the needle penetrates through the vessel wall. The flexible filament can again couple the first and second fittings, here allowing both fittings to be withdrawn along a single needle path so that the suture advances down along the first needle path, laterally across the puncture, and then out the other needle path.

Positioning of the fittings is generally effected by articulating an elongate foot within the blood vessel so that the foot extends along the vessel axis. A confirmation lumen may extend along a shaft supporting the foot to ensure that the foot is positioned within the vessel prior to articulation. Once the foot is properly articulated, it can be drawn proximally to firmly engage the endothelial layer of the vessel. The foot will preferably include tapering depressions which direct the advancing needle toward the fitting, and the suture or other flexible filament adjacent the fittings will often be releasably restrained within a narrow slot extending from the depression. The suture or other flexible filament and its associated slot will preferably be arranged to avoid entanglement of the advancing needle in the suture, and to ensure that the fitting and suture can be withdrawn proximally as the needle is retracted. An atraumatic, flexible monorail guidebody may extend from the shaft and/or the articulatable foot to facilitate alignment of the foot with the vessel, and also to help provide hemostasis while the knot is tied. A wide variety of foot articulation mechanisms may be provided, with deployment preferably being effected when the foot is disposed entirely within the vessel and using an actuator and foot motion that avoid dilation of the puncture.

In another aspect, the invention provides a method for suturing an opening in a tissue. The method comprises inserting a distal end of a probe through the opening, the probe defining a probe axis. An elongated foot of the probe is articulated so that first and second ends of the foot extend laterally with the opening aligned therebetween. A first needle path is formed from the probe, through the tissue, and to the first end of the foot. A second needle path is formed from the probe, through the tissue, and to the second end of the foot. Suture is advanced along the first and second needle paths to position a suture loop across the opening.

In another aspect, the invention provides a method for suturing a blood vessel. The vessel has a vessel wall, and the method comprises advancing a shaft toward the vessel wall. The shaft has an axis and a plurality of needle guides. A foot is deployed adjacent the vessel wall so that the foot extends laterally from the shaft. A plurality of needles are advanced from the needle guides of the shaft to the foot to form needle paths through the vessel wall. The needle guides deflect the needles laterally so that a needle path width between the needles is greater than a cross-sectional dimension of the shaft. Suture is advanced along the needle paths to position at least one suture loop across the puncture.

In yet another method of the present invention, a blood vessel is sutured through a tissue tract of a patient body. The vessel has a vessel wall, and the method comprises inserting a distal end of a probe through the puncture and into the blood vessel. A first end of the suture is advanced from the probe within the tissue tract, through the vessel wall, and into the vessel. The first end of the suture is withdrawn from the vessel through the vessel wall, and through a bight of the suture to form a loop of suture across the puncture. The first end of the suture and a second end of the suture adjacent the bight are tensioned to detach the bight from the probe and form a knot affixing the loop of suture across the puncture. Advantageously, the bight of suture may be pre-tied before the probe is inserted into the tissue tract, the bight optionally being releasably attached to the probe.

In a device aspect, the invention provides a system for suturing a blood vessel. The vessel has a vessel wall, and the system comprises a needle having a proximal end and a distal end suitable for forming a needle path through the vessel wall. The needle has a recessed engagement surface adjacent the distal end. The system further comprises a flexible filament and a fitting attached to the filament. The fitting has an opening and a tab extending into the opening, the tab securingly engaging the engagement surface when the needle advances through the vessel wall and into the opening, so that the fitting and at least a portion of the filament can be withdrawn proximally along the needle path by the needle.

In a further device aspect, the invention provides a system for suturing a puncture of a blood vessel within a tissue tract. The vessel has a vessel wall and defines an axis, and the system comprises a shaft having a proximal handle and a distal end suitable for insertion along the tissue tract and into the vessel through the puncture. A foot is mounted near the distal end of the shaft. The foot has plurality of needle receptacles extendable laterally from the shaft. A flexible filament extends between the receptacles of the foot. A plurality of needles are advanceable distally and laterally from the shaft, through the vessel wall outside the puncture, and to the receptacles of the foot.

In yet another device aspect, the invention provides a system for suturing a puncture of a blood vessel within a tissue tract. The vessel has a vessel wall, and the system comprises a shaft having a proximal handle and a distal end suitable for insertion along the tissue tract and into the vessel through the puncture. A foot is mounted near the distal end of the shaft. The foot has a first needle receptacle and is articulatable from a small profile configuration to a large profile configuration by actuation of the handle. A first fitting is removably mounted adjacent the first needle receptacle. A filament is coupled to the first fitting. A first needle is advanceable from the shaft to the first needle receptacle on the articulated foot. The first fitting securely engages the first needle so that the secured first fitting and at least a portion of the filament can be drawn through the vessel wall by the first needle.

In a still further device aspect, the invention provides a probe for suturing an opening in a tissue. The probe comprises a shaft having a proximal end and a distal end and defining an axis therebetween. The shaft has a size and configuration suitable for insertion through the opening in the tissue. An elongate foot is movably mounted to the shaft. An actuator extends along the shaft distally to the foot. Movement of the actuator slides the foot axially and pivots the foot from a low profile configuration to a deployed configuration extending laterally from the shaft. A suture is supported by the foot, and a needle is advanceable from the shaft, through the tissue, and to the deployed foot.

In another aspect, the invention provides a suturing device having a first penetrator and a second penetrator for suturing an incision. The first penetrator is configured to form a first penetration about a periphery of the incision. The first penetrator also carries a pre-tied knot disposed about a periphery of the first penetrator for delivery to the incision. The second penetrator is configured to form a second penetration about the periphery of the incision. The second penetrator also includes suture disposed thereon that is drawn by the first penetrator through the first penetration and through the pre-tied knot during retraction of the first and second penetrators from around the periphery of the incision. The first penetrator draws the suture through the first penetration via a connection between the first penetrator and the suture. Moreover, as the first penetrator draws the suture, the suture delivers the pre-tied knot to the incision for closure of the incision.

In another aspect, the invention provides a suturing device for suturing an incision formed in an artery. The suturing device includes a first penetrator, a second penetrator and a receiver. The first penetrator, which forms a first penetration about a periphery of the incision, includes a pre-tied knot disposed about the first penetrator. The second penetrator, which forms a second penetration about the periphery of the incision, has suture disposed thereon, which retracts through the first penetration. The suture retracts through the first penetration into the pre-tied knot during retraction of both the first penetrator and the second penetrator from around the periphery of the incision. In addition, during retraction, the suture delivers the pre-tied knot to the incision for suturing of the incision. The suturing device also includes a receiver for receiving both the first penetrator and the second penetrator upon penetration formation. The receiver connects the suture to both the first penetrator and the second penetrator and allows retraction of the suture through the first penetration as the first penetrator and the second penetrator retract.

In another aspect, the invention provides a suturing device for suturing an opening of an artery of a patient during a surgical procedure. The suturing device includes a first penetrator, a second penetrator and a foot. The first penetrator is disposed about a periphery of the suturing device and the second penetrator is located opposite the first penetrator on the suturing device. The first penetrator includes a pre-tied knot configured to receive suture releasably engaged with the second penetrator during suturing of the opening of the artery. The foot, which is movably coupled to the suturing device distal to the first penetrator and the second penetrator, includes a first cuff and a second cuff. The first cuff and the second cuff, which couple to one another via a link, receive the first penetrator and a detachable end of the second penetrator respectively. The first and second penetrators penetrate the artery at a proximal end of the suturing device and couple with the first cuff and the second cuff upon penetration of the artery. The first and second penetrators couple with the first cuff and second cuff such that during retraction of the first penetrator and the second penetrator from the artery, the suture delivers the pre-tied knot to the incision for closure of the incision.

In various aspects and embodiments of the invention described herein, a pre-tied knot of suture is also included. The pre-tied knot may initially be positioned wrapped around an exterior surface of the device. Specifically, a length of suture having opposite ends and a bight of suture therebetween is provided with the bight being disposed around an exterior surface of the device.

In other aspects and embodiments described herein, a suture cutting blade is positioned on the device. The suture cutting blade provides a convenient cutting edge across which the suture can be drawn to sever the suture from the needle.

Another aspect and embodiment described herein is to provide an improved activation mechanism for the suturing device, which provides an improved ergonomic design that results in greater control and ease of use for the user.

Yet another aspect is to provide alignment guides to assist in the placement and rotational orientation of a suture relative to the vessel opening, to facilitate the use of multiple sutures with different angular orientations, as necessary, to close vessel punctures.

BRIEF DESCRIPTION OF THE DRAWINGS

FIG. 1 is a perspective of a percutaneous blood vessel closure device according to the principles of the present invention.

FIGS. 4 and 4A are perspective views illustrating a suture attachment cuff and an associated barbed needle for use in the vessel closure device of FIG. 1.

FIG. 5 is a cross-sectional view showing the barbed needles securingly engaging the suture cuffs of the deployed foot.

DETAILED DESCRIPTION

Figure 2A:
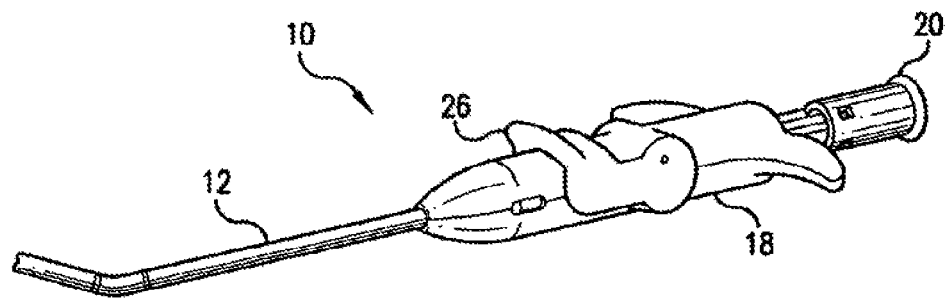
FIGS. 2A-C illustrate actuation of a foot and advancement of needles from a shaft to the articulated foot in a probe similar to the probe of FIG. 1.

Several embodiments of suturing device that delivers a pre-tied knot to a puncture or incision in a wall of tissue is disclosed. Various aspects of such a device include a length of suture having a bight between first and second ends of the suture. The bight includes one or more loops of suture that form a pre-tied knot when one or more ends of the suture are advanced through the bight. The bight of suture may be prearranged in any of several configurations on the device.

Referring now to FIG. 1, a vessel closure device 10 generally has a shaft 12 having a proximal end 14 and a distal end 16. A proximal housing 18 supports a needle actuation handle 20. A flexible, atraumatic monorail guidebody 22 extends distally of distal end 16 of shaft 12.

Figure 2B:
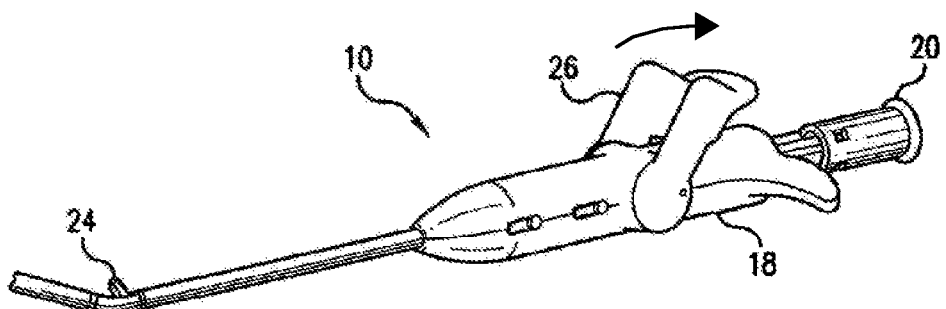
Figure 2C:
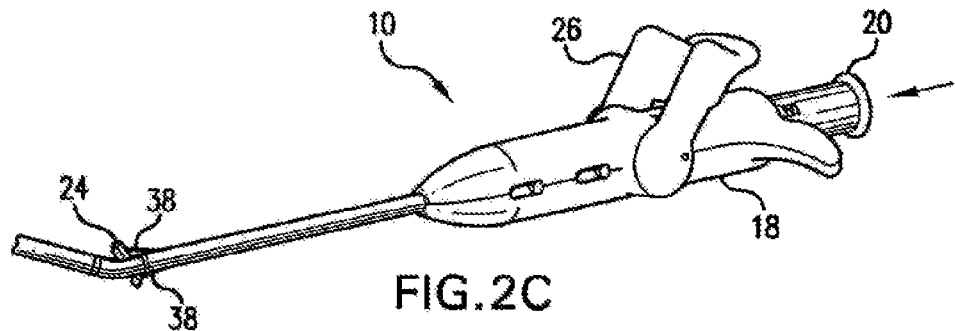

As can be seen with reference to FIGS. 2A through C, a foot 24 is articulatably mounted near the distal end of shaft 12. Foot 24 moves between a low profile configuration, in which the foot is substantially aligned along an axis of shaft 12 (as illustrated in FIG. 1), to a deployed position, in which the foot extends laterally from the shaft, upon actuation of a foot actuation handle 26 disposed on proximal housing 18.

FIGS. 2A through C illustrate the structure and actuation of foot 24 of an embodiment of probe 10, and also show how needles 38 can be advanced distally from shaft 12 to the foot by depressing needle actuation handle 20 (see FIG. 2C).

Figure 3A:
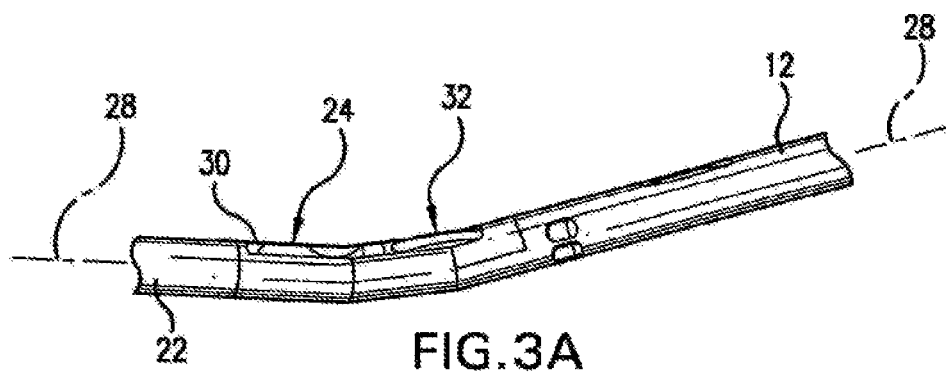
FIG. 3A is a detailed view showing the foot of the vessel closure device of FIG. 1 in a parked position prior to deployment.

Actuation of foot 24 is illustrated more clearly in FIGS. 3A and B. In the parked position illustrated in FIG. 3A, foot 24 extends substantially along axis 28 of shaft 12. Note that the axis of the shaft need not be straight, as the shaft may curve somewhat, particularly adjacent the foot. In the exemplary embodiment, foot 24 is substantially disposed within a foot receptacle 30 of shaft 12 to minimize the cross-section of the device adjacent the foot prior to deployment. Advantageously, prior to deployment of the foot, device 10 can have a cross-section adjacent foot 24 of about 7 Fr or less, ideally having a cross-section of about 6 Fr or less for the entire device distally of the proximal end 14 of shaft 12.

Figure 3B:
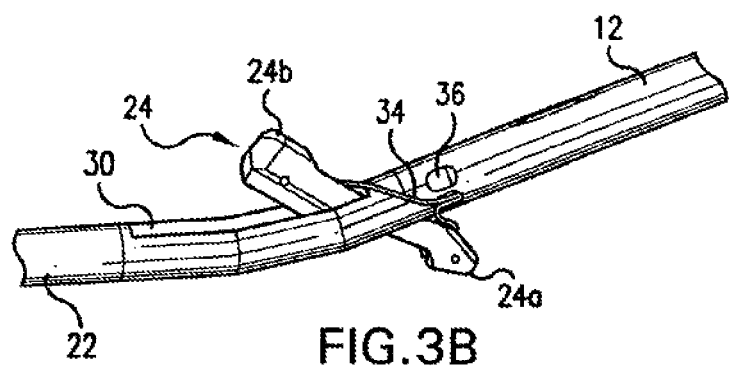
FIG. 3B is a detailed view showing the foot of the vessel closure device of FIG. 1 in a deployed position.

Actuation of foot handle 26 slides a foot actuation wire 32 proximally, pulling foot 24 from a parked position to the deployed position illustrated in FIG. 3B. Once deployed, a first end 24a and a second end 24b of foot 24 extend laterally from the shaft. Suture 34 here comprises a continuous filament with ends disposed in needle receptacles adjacent each end of the foot. An intermediate portion of suture 34 may extend proximally along a suture lumen of shaft 12 to and/or beyond proximal housing 18. Alternatively, the length of suture between the ends may extend distally within flexible guidebody 22, preferably in a dedicated lumen (separate from the monorail guidewire lumen). In still further alternatives described below, a short length of suture or some other flexible filament may extend substantially directly between the needle receptacles.

Shaft 12 also includes a foot position verification lumen that extends distally from a position verification port 36 to a position indicator at housing 18. When the foot is properly positioned within the blood vessel, blood pressure will cause blood to flow proximally through the indicator lumen to the indicator. The indicator may optionally comprise a blood exit port, a clear receptacle in which blood is visible, or the like. In the exemplary embodiment, the indicator of handle 18 comprises a length of clear tubing extending from housing 18 (not shown) in which the blood is clearly visible. It should be understood that a wide variety of alternative position verifications sensors might be used, including electrical pressure sensors, electrolytic fluid detectors, or the like.

The structures used in positioning a loop of suture across the puncture can be understood with reference to FIGS. 4, 4A, and 5. In general terms, needles 38 extend from shaft 12 into secured engagement with fittings 40 attached to sutures 34. More specifically, needles 38 include a barbed end 42 defining a recessed engagement surface 44. Fittings 40 are roughly cylindrical structures having an axial channel 46 which receives barbed end 44 of needle 38 therein. A first slot is cut in fitting 44 to define at least one tab 48. Tabs 48 can be resiliently biased inward into channel 46. As needle 38 advances into fitting 40, barbed end 42 resiliently displaces tab 48 clear of channel 46 to allow the barbed end to pass axially into the fitting. Once barbed end 42 is disposed axially beyond tab 48, the tab resiliently flexes back into the channel, capturing needle 38 by engagement between the tab and recessed surface 44. As each tab can hold the fitting in place on the needle, the use of more than one tab increases the reliability of the system. Ideally, three tabs are provided, as illustrated in FIG. 4A.

To facilitate attachment of fitting 40 to suture 34, a second slot cut in the tubular fitting structure defines a suture attachment collar 50. Optionally, collar 50 may be crimped about suture 34 to mechanically affix the suture to fitting 40. In addition and/or instead of mechanical crimping, suture 34 may be bonded to fitting 40 using an adhesive, heat, fasteners, knots, or the like.

Fitting 40 is quite small in size, and is generally configured to facilitate withdrawing the fitting (and the attached suture) along with needle 38 axially through the vessel wall along the needle path. Needle 38 will generally have a cross-sectional width of between about 0.010 inches and 0.020 inches. Barb 42 will extend laterally to define an engagement surface 44 having a protruding length of between about 0.002 inches and 0.005 inches. Fitting 40 will preferably have a cross-sectional size roughly corresponding to or only slightly larger than needle 38. Fitting 40 will typically have an outer lateral width of between about 0.014 inches and 0.025 inches, and an axial length of between about 0.035 inches and 0.050 inches. Channel 46 will be sized to receive at least a portion of needle 38, and will generally have a width of between about 0.010 inches and 0.020 inches. Suture 34 will preferably extend axially opposite the open end of channel 46 to minimize drag when the suture is drawn proximally along the needle path. In the exemplary embodiment, needle 38 has a diameter of about 0.020 inches, while the fitting comprises a tube having an outer diameter of about 0.020 inches, an inner diameter of about 0.016 inches, and an overall length of about 0.047 inches. The fitting will typically comprise a resilient material, preferably comprising a metal, and in the exemplary embodiment, comprising stainless steel.

Needles 38 typically have a length of between about 5.0 inches and 6.0 inches, and will preferably be sufficiently stiff to be advanced in compression through the vessel wall (and adjacent tissues) for up to 0.5 inches when supported in cantilever. Nonetheless, the needles will ideally be flexible enough to be laterally deflected within shaft 12, as can be understood with reference to FIG. 5. Needles 38 generally comprise a high strength metal, ideally comprising stainless steel. Fittings 40 will also preferably comprise a flexible material to allow tab 48 to flex out of the way of barbed end 42, and to resiliently rebound and engage recessed surface 44. In the exemplary embodiment, barbed end 42 has a diameter of about 0.015 inches, with the diameter of the needle decreasing to about 0.008 inches proximally of the barb to define the recessed engagement surface.

As was generally described above, foot 24 includes needle receptacles 52 adjacent the ends of the foot. A fitting 40 (with an associated end of suture 34) is disposed within each needle receptacle, and a surface of the receptacle tapers proximally and outwardly so as to guide the advancing needles 38 into engagement with fittings 40 when foot 24 is in the deployed position. As fittings 40 (and associated portions of suture 34) are releasably supported in the foot, needles 38 can be withdrawn proximally so as to draw the fittings and suture ends from the foot proximally into (and optionally through) shaft 12. The needle receptacles of the exemplary embodiment taper outward at an angle between 20 and 35 degrees from the centerline of fitting 40, and the fitting is held in a recess having a diameter of about 0.0230 inches and a length of about 0.042 inches. A lateral opening or window through the side of foot to the fitting recess may be provided to facilitate needle and/or cuff positioning during assembly of the probe, and a protruding collar near the proximal end of the fitting recess may help keep the fitting in position.

A wide variety of foot actuation mechanisms might be used within the scope of the present invention.

FIG. 5 also illustrates the lateral deflection of needles 38 by needle guides 54 of shaft 12. This lateral deflection of the needles allows the use of a small diameter shaft, while still encompassing sufficient tissue within the suture loop on opposite sides of the puncture to effect hemostasis when the suture looped is tightened and secured. In the exemplary embodiment, shaft 12 comprises an outer casing of a biocompatible material such as stainless steel, carbon fiber, nylon, another suitable polymer, or the like. Needle guides 54 may be defined at least in part as lumens formed within the casing of a polymeric material such as nylon or the like. In some embodiments, shaft 12 may comprise a carbon fiber filled nylon, or carbon fiber filled with an alternative material.

Figure 6A:
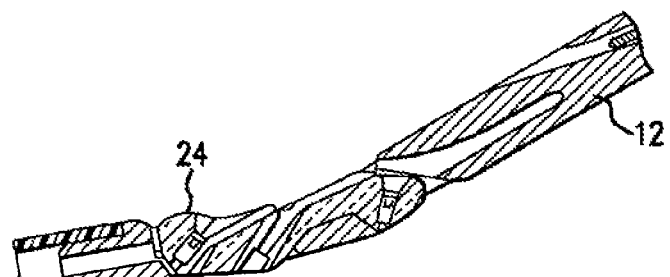
FIGS. 6A-C illustrate one embodiment of a deployable foot, in which the foot slides and pivots when drawn proximally by a tension member.
Figure 6B:
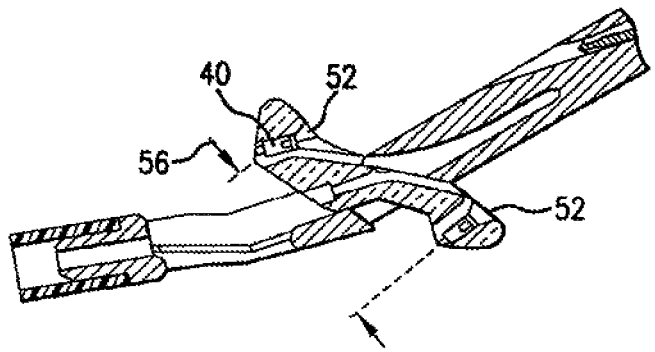
Figure 6C:
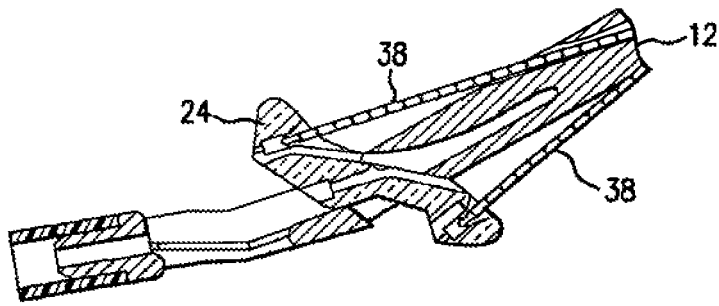

One example of a suitable structure and articulation motion for foot 24 is illustrated in FIGS. 6A and B. Foot actuation wire 32 (see FIG. 3A) rides in a lumen of shaft 12, and draws foot 24 from a parked position (shown in FIG. 6A) to a deployed position (shown in FIG. 6B) through a combination of sliding and pivoting of the foot. The foot remains supported throughout its range of motion by arms disposed laterally on either side of the foot, the arms defining (at least in part) foot receptacle 30. Once foot 24 is deployed, needle receptacles 52 and/or the fittings disposed therein will preferably define a lateral suturing width 56 in a range from about 0.260 inches to about 0.300 inches. Foot 24 may be machined or cast from a polymer or metal, but will preferably comprise a polymer such as carbon fiber or glass-filled nylon or suitable reinforcement material. In some cases, foot 24 may be molded as two separate halves which can subsequently be affixed together. Needles 38 advance from the fixed needle guides 54, and are laterally directed into fittings 40 by receptacles 52, as illustrated in FIG. 6C. In general, a shape memory alloy such as Nitinol® in its superelastic regime provides a particularly advantageous actuator wire for manipulating foot 24. A wide variety of foot designs and foot actuation mechanisms can be used within the scope of the invention.

Figure 7:
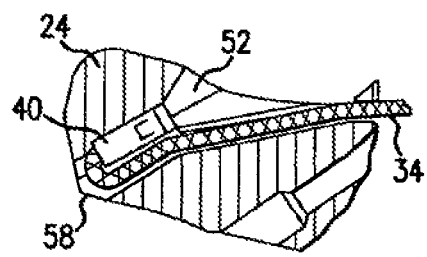
FIG. 7 illustrates the suture cuff positioned within a needle receptacle, and also shows how the suture is releasably secured within a slot extending radially from the needle receptacle.

Referring now to FIG. 7, fittings 40 and suture 34 will be withdrawn proximally by the needles from needle receptacles 52. To releasably support fittings 40 and suture 34 and avoid entanglement of the suture in the needles, suture 34 is fittingly received within a slot 58 which extends laterally from needle receptacles 52. As the needles pull the fitting axially from needle receptacles 52, suture 34 is pulled from slot 58 and free from foot 24. Bending of the suture proximally within the suture slot can also locally increase the suture width, so that the interaction between the bent suture and the slot can help hold the fitting in the recess.

Figure 8A:
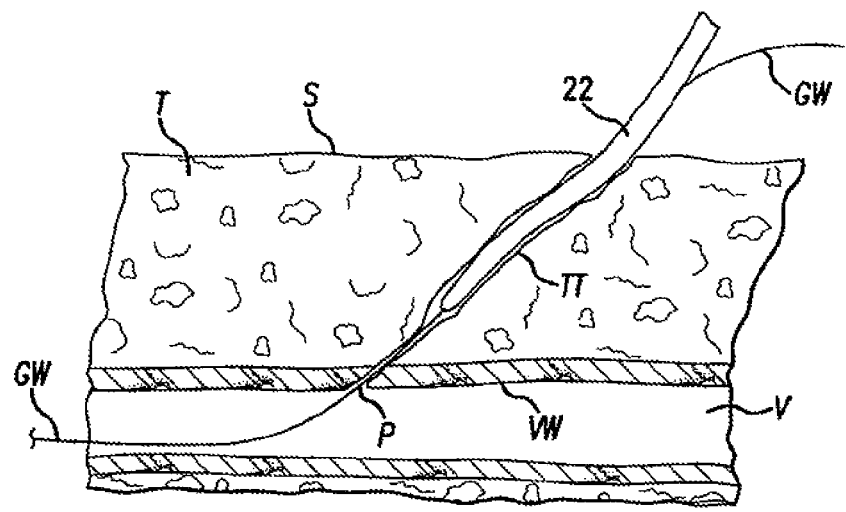
FIGS. 8A-G illustrate a method for use of a suture system to effect hemostasis of a blood vessel puncture through a tissue tract.
Figure 8B:
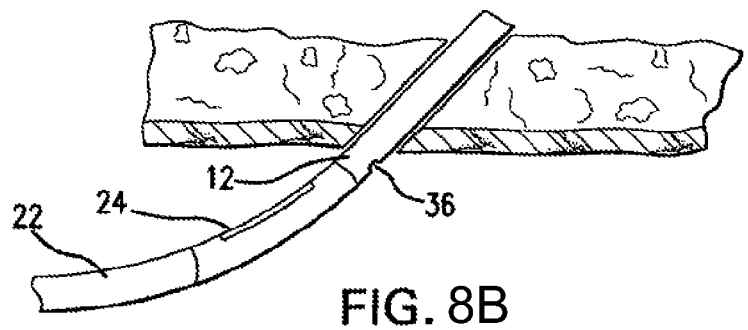

The operation and use of probe 10 can be further understood with reference to FIGS. 8A-G. After accessing a blood vessel V (often using the Seldinger technique), a guidewire GW is left extending into skin S and down through tissue T along tissue tract TT. Guidewire GW enters vessel V through a puncture P in vessel wall W, and extends along the vessel throughout many endovascular procedures. As illustrated in FIG. 8A, distal guidebody 22 is advanced over the guidewire GW in a monorail fashion, so that the guidewire helps to direct the probe along the tissue tract TT and into the vessel through puncture P. FIG. 8B shows that when sensor 36 is disposed within the vessel, blood can flow from the sensor port and through a lumen in shaft 12 to the proximal handle to notify the operator that foot 24 has been advanced far enough for deployment.

Figure 8C:
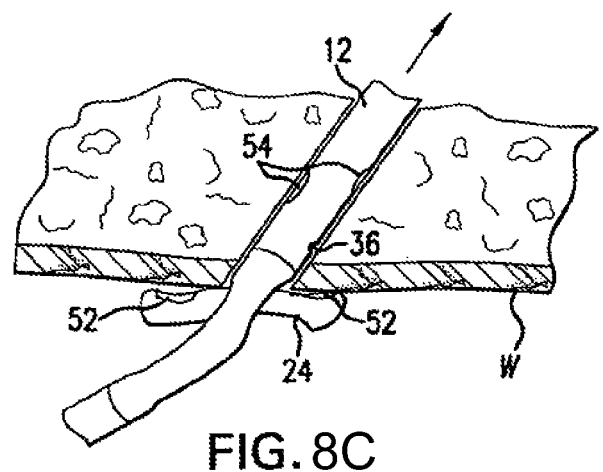

Deployment of the foot is effected by actuation of the foot deployment handle 26, as described and illustrated above with reference to FIGS. 2, 2B and 3B. As described above, guidebody 22 helps to align the probe with the axis of vessel V. Guidebody 22 may be set at an angle and/or offset relative to shaft 12 as appropriate to aid in alignment with a particular vessel access technique. As shown in FIG. 8C, the deployed foot 24 extends laterally from the shaft, so that foot 24 adjacent receptacles 52 can be drawn up against vessel wall W by gently pulling shaft 12. Hence, the foot helps to accurately position the needle guides 54 at a distance from the vessel wall.

Figure 8D:
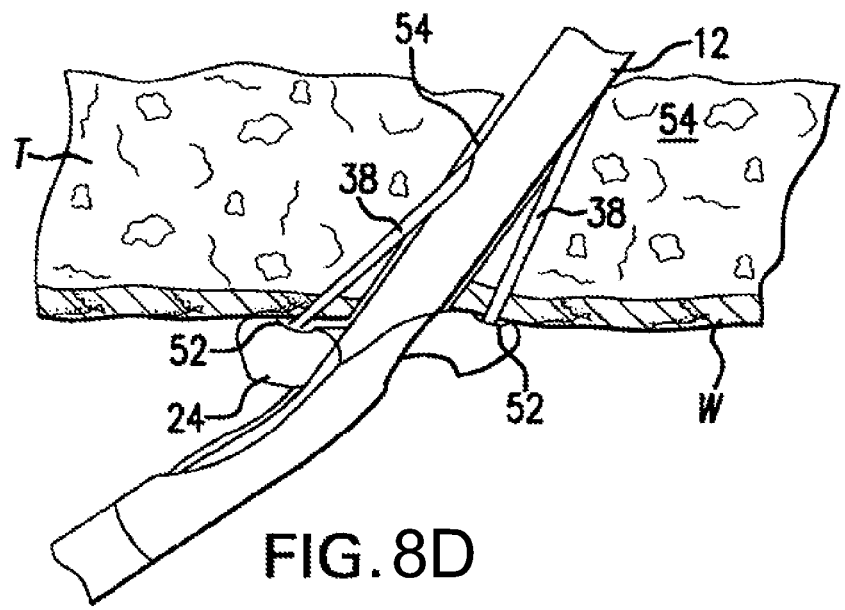

Referring now to FIG. 8D, once foot 24 is properly positioned against the inner surface of the vessel wall, flexible needles 38 can be advanced through the vessel wall by depressing needle actuator handle 20, thereby advancing needle actuator handle 20 and flexible needles 38 in a distal direction. As they are advanced distally, flexible needles 38 are deflected laterally by needle guides 54 toward receptacles 52 of the deployed foot. As a result, the needles advance in cantilever both distally and laterally when needle actuation handle 20 is pressed (see FIG. 2C), and the tapering surfaces of receptacles 52 help to push the needles back into alignment with the fittings so as to overcome any unintended deflection of the needles by tissue T or vessel wall W. This ensures that needles 38 securingly engage fittings 40 within receptacles 52 (see FIGS. 5, 6C and 7), thereby coupling the ends of suture 34 to the needles. While suture 34 is here illustrated running along the side of shaft 12 outside foot receptacle 30 to a lumen within guidebody 22, it should be understood that the suture loop might instead extend proximally in a lumen of shaft 12, might be routed through the foot and/or foot receptacle, and/or might be stored in a spool adjacent foot 24. Regardless, suture 34 should able to pull free of the probe between its ends to form a continuous loop across puncture P.

Figure 8E:
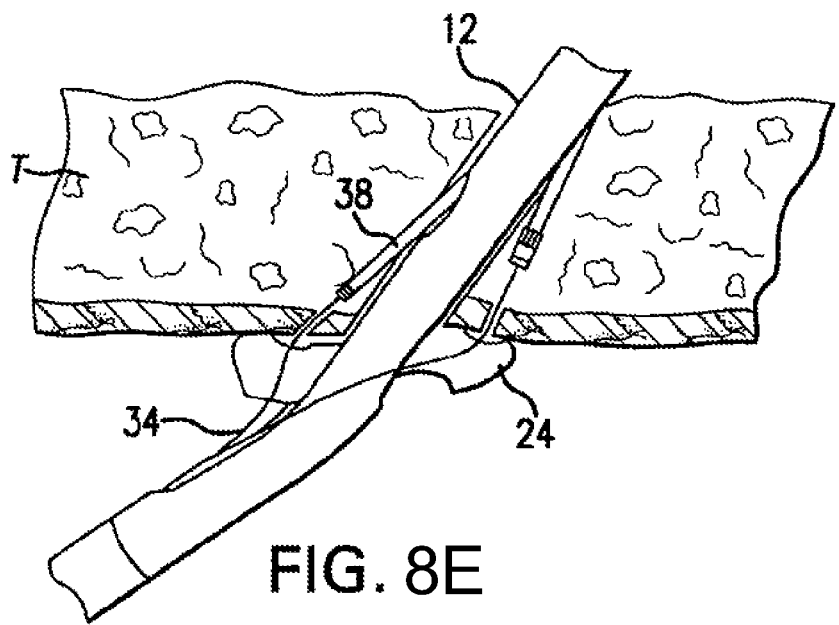
Figure 8F:
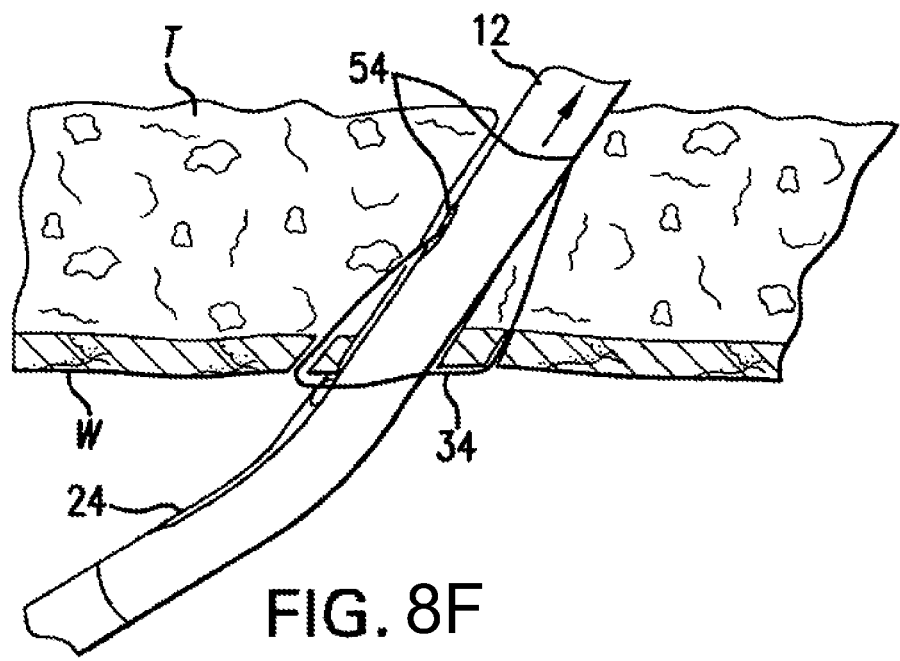

Referring now to FIGS. 8E and F, once the needles 38 have been fully advanced into, and engage, fittings 40, the needles 38, with fittings 40 and suture 34 now attached to the ends of needles 38, can then be withdrawn proximally by pulling on needle actuation handle 20 (FIG. 2C) in a proximal direction. Fittings 40 and the ends of suture 34 are drawn proximally through the vessel wall W along the needle paths formed by needles 38. Optionally, the needles may be withdrawn proximally out of the tissue tract and clear of shaft 12, or they may remain coupled to the shaft within needle guides 54.

Once the needles 38 are withdrawn into the needle guides, the foot actuator 26 is moved to store foot 24 along shaft 12, and the shaft can then be pulled proximally from the tissue tract. Guidebody 22, which may comprise a soft, compliant polymer, may temporarily extend at least partially into tissue tract TT and through puncture P to help reduce the loss of blood until the loop is secured.

Figure 8G:
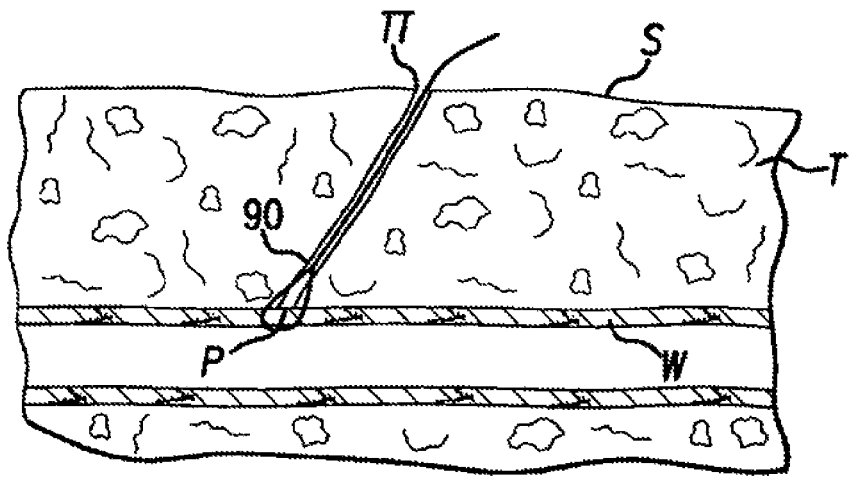

Now referring to FIG. 8G, once shaft 12 has been withdrawn sufficiently to expose needle guides 54, the ends of the suture loop can be grasped by the operator. Tying of a knot in suture 34 can then proceed in a conventional manner. The use of a clinch knot may facilitate gradual tightening of the knot while removing guidebody 22, although a wide variety of knot and knot advancing techniques might be used.

Figure 9:
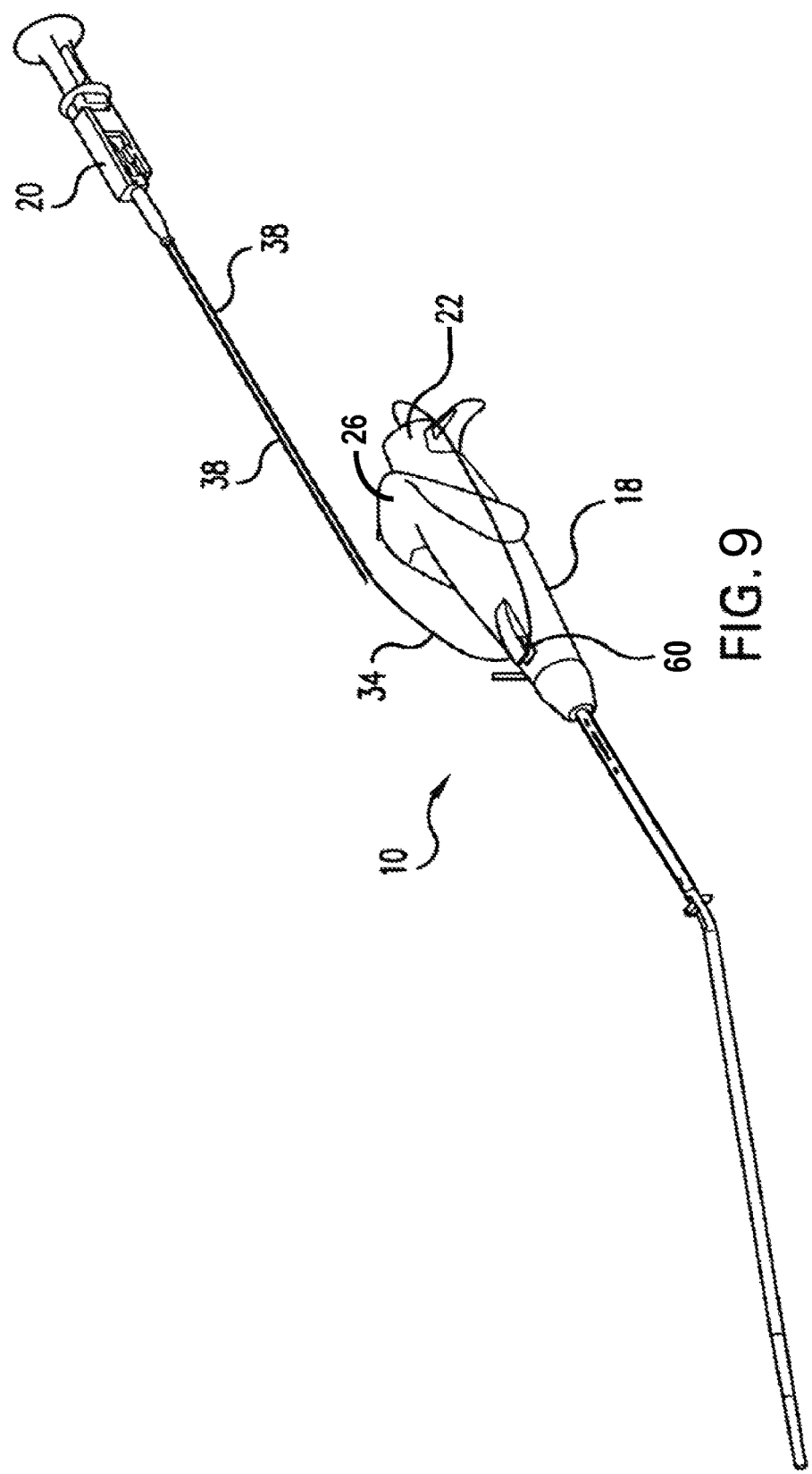
FIG. 9 is a perspective view of a suturing device including a suture cutting blade positioned on the device.

As shown in FIG. 9, the suturing device 10 may also include a blade 60 positioned on the device to provide a convenient cutting edge to sever the suture to detach the suture from the needle or needles. FIG. 9 shows a suturing device 10 of the type having an articulated foot described herein. The suturing device 10 is particularly useful for suturing an opening in a femoral artery of a patient after the completion of a percutaneous transluminal catherization procedure, or the like. Suturing device 10 is an example of the type of device that may include a blade 60 positioned on the device. For convenience of description, only this suturing device embodiment will be described with respect to the suture cutting blade feature. It is to be understood, however, that any suturing device employing a needle and suture to close an opening in a tissue wall may incorporate the suture cutting blade feature described more fully below.

The suturing device 10 shown in FIG. 9 includes a housing 18. One or more needles 38 are operatively associated with the device. The needles 38 are movable with respect to the housing 18. The needles 38 are shown in FIG. 9 withdrawn from the housing 18. In this exemplary embodiment, only one of the two needles 38 are shown attached to a length of suture 34. In other embodiments, both needles may be attached to the suture 34. Alternatively, the device may only include one needle.

Figure 14A:
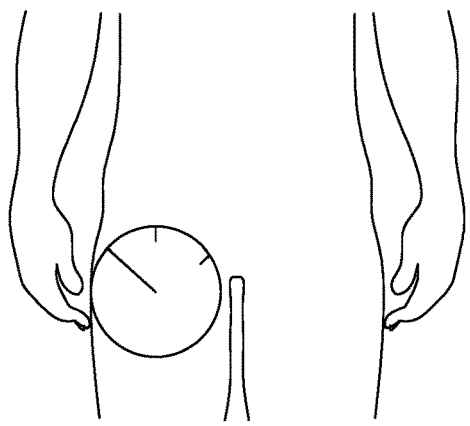
FIGS. 14A-C are schematic representations of different angular orientations that can be achieved through the use of the multiple alignment markings of the device.
Figure 14B:
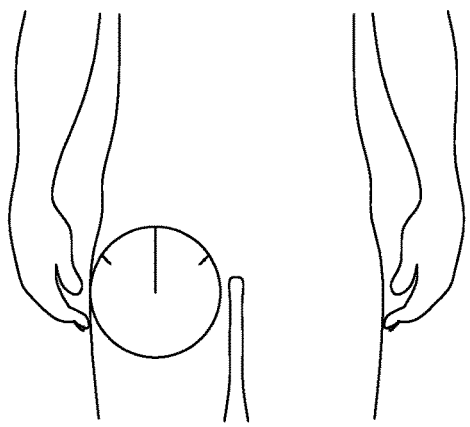

A suture cutting blade 60 is positioned on the device 10 such that when the needle 38 and attached suture 34 are withdrawn from the device, the suture 34 can be drawn across the blade 60 to sever the suture. FIG. 9 shows the position of the needle and suture with respect to the housing 18 and the blade 60 just prior to the suture being cut to detach the needle 38 from the length of suture. As can be seen in FIG. 14, a portion of the suture may remain attached to the needle 38 due to the suture being cut at a short distance from the end of the needle. The length of suture that is used to close the opening in the tissue will be detached from the needle or needles. Once the needle 38 is cut away from the length of suture that has been withdrawn from the proximal end 22 of the housing 18, the device 10 can be removed from the patient's anatomy without interference from the needle actuation handle 20.

Additional details regarding such articulating suturing devices and methods are provided in: U.S. patent application Ser. No. 15/090,150, filed Apr. 4, 2016, and entitled "Articulating Suturing Device and Method;" U.S. patent application Ser. No. 14/195,308, filed Mar. 3, 2014, and entitled "Articulating Suturing Device and Method;" U.S. patent application Ser. No. 12/334,077, filed Dec. 12, 2008, and entitled "Articulating Suturing Device and Method," now U.S. Pat. No. 8,663,248; U.S. patent application Ser. No. 10/660,288, filed Sep. 11, 2003, and entitled "Articulating Suturing Device and Method," now U.S. Pat. No. 8,137,364; U.S. patent application Ser. No. 10/652,182, filed Aug. 29, 2003, and entitled "Articulating Suturing Device and Method," now U.S. Pat. No. 7,235,087; U.S. patent application Ser. No. 10/152,272, filed May 20, 2002, and entitled "Articulating Suturing Device and Method," now U.S. Pat. No. 6,964,668; U.S. patent application Ser. No. 09/651,344, filed Aug. 29, 2000, and entitled "Articulating Suturing Device and Method," now U.S. Pat. No. 7,001,400; and U.S. patent application Ser. No. 09/262,402, filed on Mar. 4, 1999, and entitled "Articulating Suturing Device and Method," now U.S. Pat. No. 6,136,010, each of which is hereby incorporated by reference in its entirety.

One issue associated with the embodiments described above is that, during use of the device 10, a user (surgeon) must reposition her or his hands several times during use. For example, it is common for the surgeon to hold the proximal end of housing 18 with one hand and to hold and stabilize the distal end of housing 18 with the other hand while advancing the device over the guidewire and inserting the device through the tissue tract. Once device 10 is inserted far enough into the vessel that blood flows into the device 10 and out of the blood sensor port (thereby indicating that device 10 is properly positioned within the vessel so as to allow foot 24 to be deployed), then the surgeon must release the distal end of housing 18, reposition her or his hand to deploy foot 24 by manipulating foot actuation handle 26. Then, it is common for the surgeon to reposition her or his hand to again stabilize the distal end of housing 18

(i) as the device is drawn proximally to position foot 24 against the inner surface of the vessel wall, (ii) as needles 38 are advanced distally to engage fittings 40, and (iii) as needles 38, fittings 40 and suture 34 are withdrawn proximally from the tissue tract. Finally, the surgeon must, once again, reposition her or his hand from the distal end of housing 18 to rotate foot actuation handle 26 in the other direction to the return foot 24 to its parked or collapsed position to permit removal of device 10. It would, therefore, be an improvement to provide a vessel closure device of the type described herein and that provides an improved ergonomic design that allows placement, actuation and removal without requiring the user to reposition her or his hands multiple times during the procedure.

Figure 10:
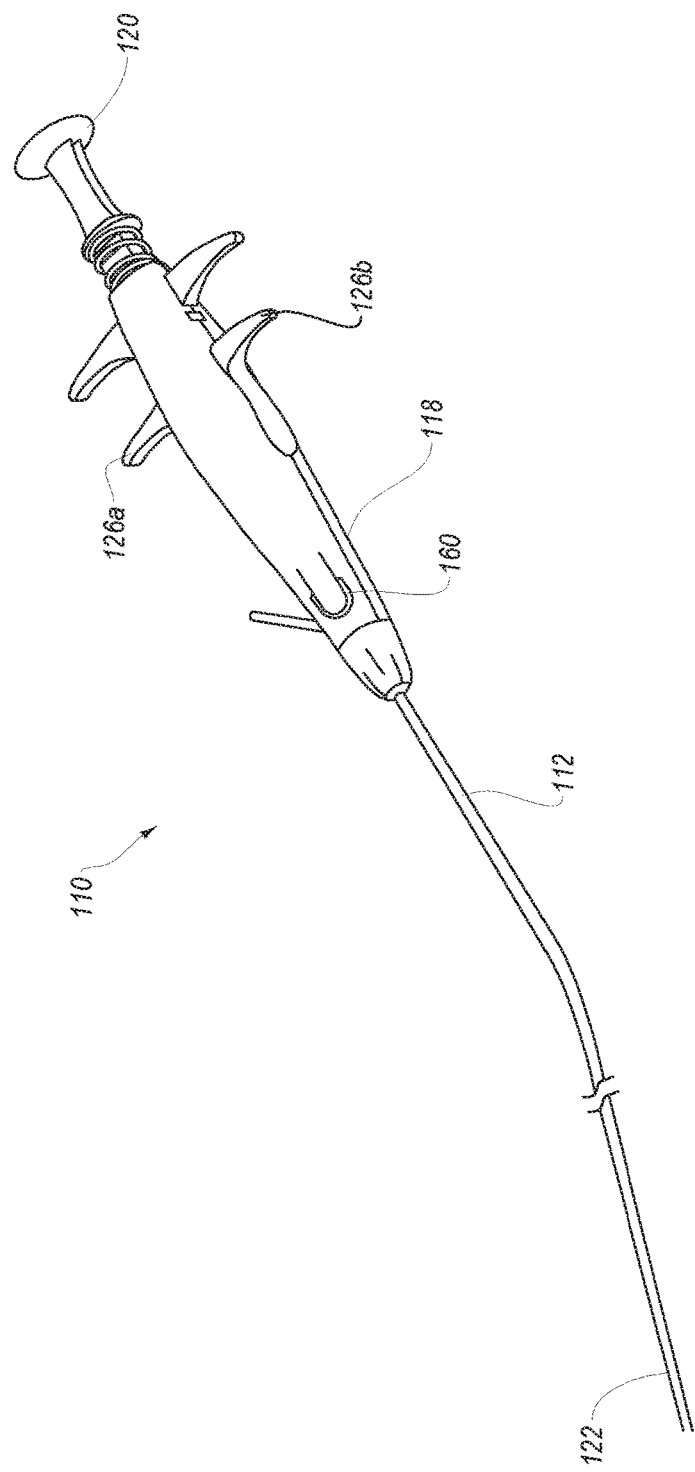
FIG. 10 is a perspective view of another embodiment of a vessel closure device.
Figure 10A:
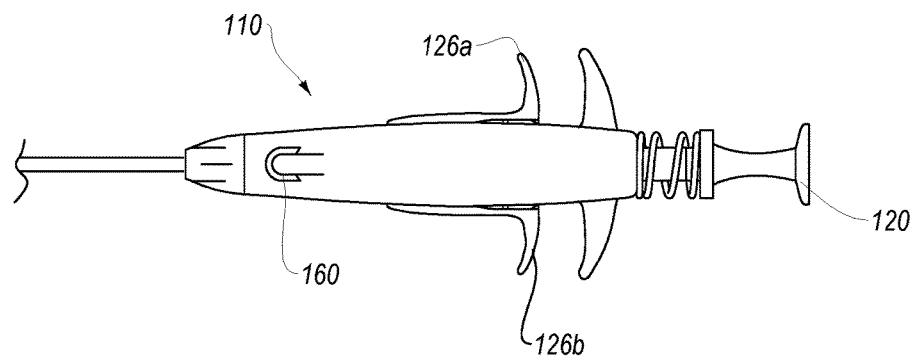
FIGS. 10A and 10B are top and side views, respectively, of another embodiment of a vessel closure device.
Figure 10B:
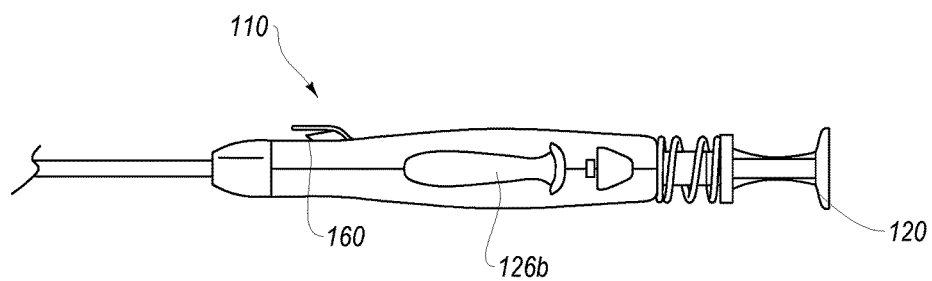
Figure 11A:
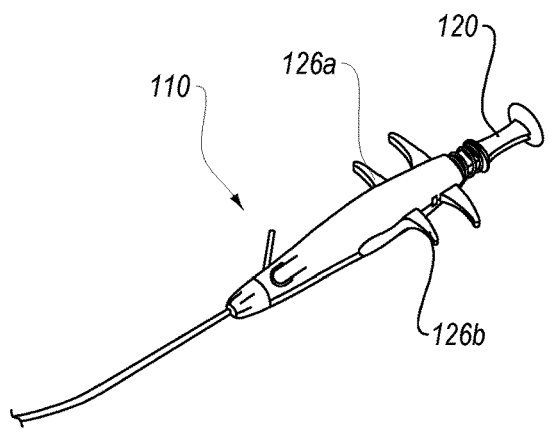
FIGS. 11A-D illustrate various steps in the operation of the vessel closure device.
Figure 11B:
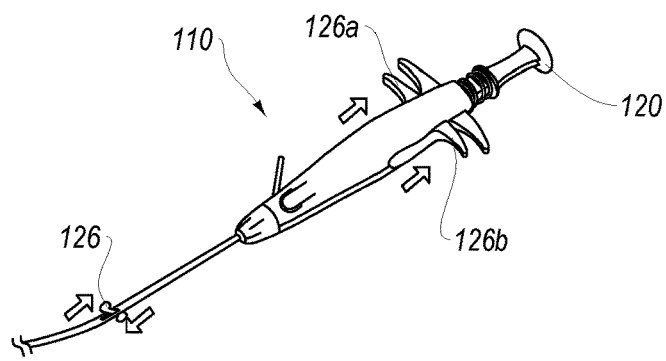
Figure 11C:
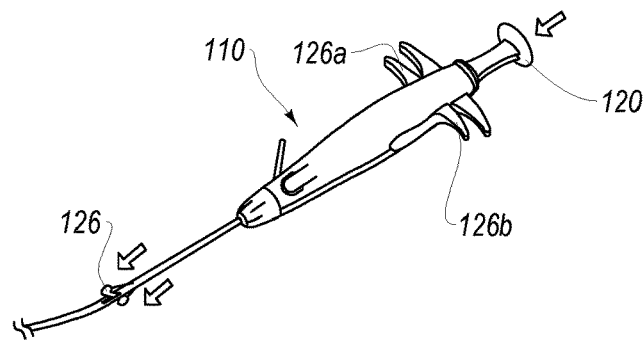
Figure 11D:
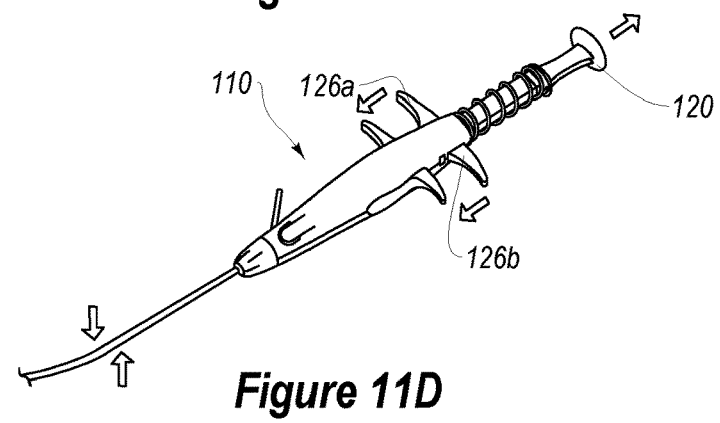
Figure 12:
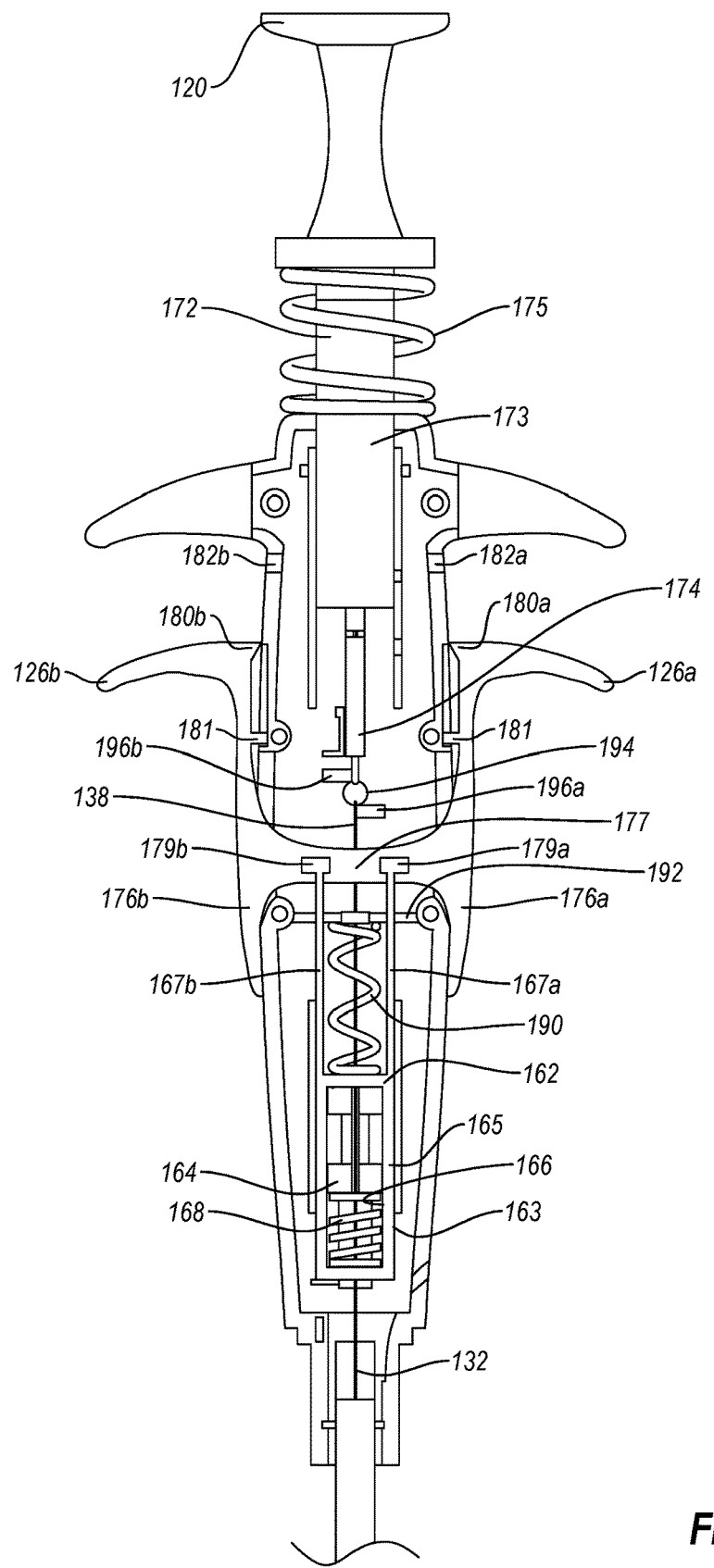
FIG. 12 is a plan view of the vessel closure device with the top of the housing removed, showing the internal components located within the proximal housing of the device.

FIGS. 10 through 12 illustrate another embodiment of an articulating suture device 110 that provides additional ease of use. Suture device 110 is similar in many respects to the embodiments illustrated and described above, and corresponding parts and features are labeled with correspondingly similar reference numerals.

One primary difference between the embodiment shown in FIGS. 1 through 14 and the embodiment of FIGS. 10 through 12 is the foot actuation handle 26. In FIGS. 1 through 14, foot actuation handle 26 is a lever that rotates about an axis that is oriented transverse with the longitudinal axis of device 10 and housing 18. As mentioned above, this design requires the surgeon to reposition her or his hands multiple times during the various steps of the procedure in order to deploy and retract the foot. As illustrated in FIGS. 10 through 12, foot actuation handle 126 consists of a pair of handles 126a and 126b that extend transversely from each side of housing 118 and move in a linear direction parallel with the longitudinal axis of housing 118. As illustrated, handles 126a and 126b can have a "trigger" configuration.

Another difference is in the operation of device 110. In particular, the embodiment makes it possible to place, actuate and remove device 110 in a substantially continuous series of actions without the need for the surgeon to reposition her or his hands in the process. As described in greater detail below, the surgeon may grasp the proximal end of housing 118 in one hand, by positioning her or his thumb on the proximal end of needle actuation handle 120 and positioning her or his index and middle fingers on foot actuation handles 126a and 126b (see FIG. 11A). In addition, the surgeon can hold and stabilize the distal end of housing 118 with the other hand. Once device 110 is properly positioned within the vessel, foot 124 is deployed by drawing foot actuation handles 126a and 126b in a proximal direction (see FIG. 11B). This is done simply by the user applying pressure between the proximal end of needle actuation handle 120 and foot actuation handles 126a and 126b, thereby drawing foot actuation handles 126a and 126b in a proximal direction relative to housing 118 and needle actuation handle 120. Once foot 124 is fully deployed, foot actuation handles 126a and 126b engage slots formed in the side of the housing to temporarily lock handles 126a and 126b into place relative to housing 118. Then, needles 138 can be deployed and advanced distally to engage foot 126 by simply applying additional pressure to needle actuation handle 120, thereby moving needle actuation handle 120 (and thus needles 138) in a distal direction relative to housing 118 (see FIG. 11C). Once needles 138 are fully advanced and engage fittings 140, the surgeon simply pulls needle actuation handle 120 in a proximal direction relative to housing 118 to draw needles 138, fittings 140 and suture 134 through the vessel wall and back into needle guides 154 (see FIG. 11D). Finally, as needle actuation handle 120 is withdrawn in the proximal direction, it automatically releases foot actuation handles 126a and 126b from their locked position, so that foot actuation handles 126a and 126b are free to return their original, starting position, thereby returning foot 124 to its parked or collapsed position (see FIG. 11D). And, all of the foregoing steps can be performed by the surgeon without having to reposition her or his hands during the entire procedure.

Referring to FIG. 12, the various components of this embodiment, and their interactions one with another, will be discussed in additional detail. Housing 118 has a bottom portion 118a and a top portion 118b. In FIG. 12, the top portion 118b has been removed and is not shown, so as to reveal various components housed within housing 118. Situated toward the distal end of housing 118 is a tensioner assembly 162 that applies a small, predetermined amount of tension to the foot actuation wire 132 when foot 124 is in a deployed position. Tensioner assembly 162 can include a sled 163 and a tensioner block 164. Sled 163 can have a rectangular portion 165, with a tensioner well 166 formed therein, and a pair of control arms 167a and 167b that extend from the proximal end of rectangular portion 165 and extend in a proximal direction. Control arms 167a and 167b can be coupled to foot actuation handle 126 in a manner described below. Tensioner block 164 and a bias spring 168 can be positioned within tensioner well 166. Tensioner block 164 can include a wire lumen 169 that extends longitudinally along the length of tensioner block 164 and is configured to receive a portion of the proximal end of foot actuation wire 132 in lumen 169. In this embodiment, foot actuation wire 132 is bonded to a portion of tensioner block 164 with a suitable bonding agent, glue or liquid cement. When the foot 124 is deployed, spring 168 is compressed a small amount between tensioner block 164 and the distal wall of tensioner well 166 to provide and maintain a small amount of tension on foot actuation wire 132 and thereby bias foot 124 to its deployed position.

Situated toward the proximal end of housing 118 is a connector assembly 172. Connector assembly 172 can include a connector 173, a follower 174 and a connector spring 175. Follower 174 can terminate at its distal end in a ball 176. Connector assembly 172 connects needle actuation handle 120 to the proximal ends of needles 138 at ball 176. As shown in FIG. 10, connector spring 175 is positioned between needle actuation handle 120 and the proximal end of housing 118 and biases needle actuation handle 120 towards its proximal, undeployed position. As further illustrated in FIG. 10, the housing can be provided with a pair of projections or fingers 196a and 196b that extend vertically from bottom housing 118a and engage opposite sides of ball 176 and on opposite sides of needles 138. Alternatively, projections 196 could also extend downward from top housing 118b, or from both bottom and top housings 118a and 118b. In any event, projections 196a and 196b initially prevent movement of needle actuation handle 120 in either direction by constraining ball 176 between projections 196a and 196b. However, projections 196a and 196b can be designed and configured to have a certain level of resilience, so that the application of a predetermined amount force to needle actuation handle 120 is required to and will cause projections 196a and/or 196b to either break or to flex to a sufficient degree to allow ball 176 to pass through, thereby allowing needle actuation handle 120 to move in a distal direction to deploy needles 138 and/or to move in a proximal direction to withdraw needles 138.

Situated between tensioner assembly 162 and connector assembly 172 is foot actuation handle 126, which forms a linkage between tensioner assembly 162 and connector assembly 172. As mentioned previously, foot actuation handle 126 can include a pair of handles 126a and 126b positioned on and extending laterally from opposing sides of housing 118. Foot actuation handle 126 can also include a pair of arms 176a and 176b that extend along opposing sides of the exterior of housing 118. Arms 176a and 178b are connected at their proximal ends to handles 126a and 126b, respectively. The other ends of arms 176a and 176b extend through slots formed in opposing sides of housing 118 and connect to a central hub 177. Central hub 177 has a lumen 178 extending through the center, through which needles 138 and follower 174 can pass. Central hub 177 can also have a pair of recesses 179a and 179b that are configured to receive the proximal ends of control arms 167a and 167b, respectively, of sled 163. With control arms 167a and 167b positioned within recesses 179a and 179b, handles 126a and 126b and tensioner assembly 162 are coupled together so that they move together in either axial direction. When handles 126a and 126b are moved in a proximal direction, this causes tensioner assembly 162 to also move in a proximal direction, thereby deploying foot 124 from a parked position to a deployed position. Conversely, when handles 126a and 126b move in a distal direction, this causes tensioner assembly 162 to also move in a distal direction, thereby causing foot 124 to move from a deployed position to a parked position.

Foot actuation handle 126 can also include a pair of lock detents 180a and 180b, located at the proximal end and on the inner surface of arms 176a and 176b, respectively. When foot actuator handle 126 is moved proximally to its deployed position, lock detents 180a and 180b engage actuator locking windows 182a and 182b, respectively, which are formed on either side of housing 118, temporarily locking foot actuator handle 126 (and, thus, foot 124) in the deployed position. Foot actuator handle 126 remains locked in the deployed position while needle actuator handle 120 is moved in a distal direction, causing needles 138 to engage fittings 140. Then, as needle actuation handle 120, needles 138, fittings 140 and suture 134 are withdrawn in a proximal direction and removed from the tissue tract, a portion of needle actuation handle 120 engages the ends of lock dents 180a and 180b, thereby releasing them from locking windows 182a and 182b and allowing foot actuation handle 126 (and foot 124) to return to the parked position. A return spring 190 is positioned within housing between a flange 192 formed in bottom housing 118a and the proximal end of sled 163. Return spring 190 biases foot actuation handle 126 toward its original, distal and parked position.

The device 110 also includes a first interlock mechanism 188 that prevents needle actuation handle 120 and/or connector assembly 178 from moving relative to the housing, either in a proximal or distal direction, while foot 124 is in its initial parked position. Once foot 124 is moved to its deployed or expanded position, then first interlock 188 automatically releases needle actuation handle 120 and connector assembly 178 to move in a distal direction relative to the housing and thereby advance needles 138 in a distal direction to engage foot 124. Similarly, with foot 124 in its deployed position, first interlock 188 also permits needle actuation handle 120 and connector assembly 178 to be withdrawn in a proximal direction relative to housing 118 and thereby withdraw needles 138, fittings 140 and suture 134 through the vessel wall and through the tissue tract. In one embodiment, first interlock mechanism 188 can include ball 176 and projections 196a and 196b, which cooperate in the manner described above to perform the functionality of first interlock mechanism 188.

Device 10 also includes a second interlock mechanism 190 that locks foot actuation handle 126 in place when it foot actuation handle 126 is moved to its position to deploy foot 124 and to thereby maintain foot 124 in its deployed position while needles 138 are advanced distally to engage fittings 140 and then withdrawn proximally from the vessel wall and tissue tract. As discussed above, once needles 138 have been withdrawn in a proximal direction far enough that the distal ends of needles 138 have been completely withdrawn into needle guides 154, then second interlock mechanism 190 automatically released foot actuation handle 126 to return to its original position, thereby returning foot 124 to its parked or collapsed position. In one embodiment, second interlock mechanism 190 can include lock detents 180a and 180b and actuator locking windows 182a and 182b, which cooperate in the manner described above to perform the functionality of second interlock mechanism 190.

Figure 13:
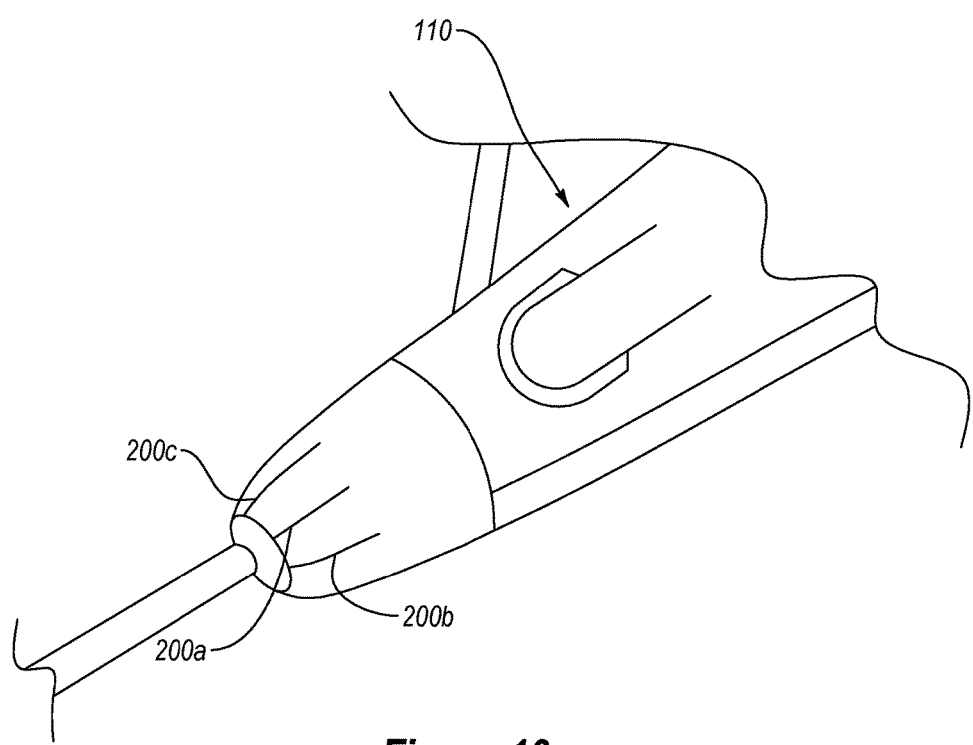
FIG. 13 is a detail view of the distal end of the housing, illustrating multiple alignment markings.

Yet an additional aspect and feature of the invention will now be discussed with reference to FIGS. 13 and 14. In some situations, such as when attempting to close a vessel puncture with a relatively large diameter, it may be desirable to apply multiple sutures across the same opening, but at different positions and/or orientations. To assist with the placement of sutures at different angular orientations relative to the puncture, the vessel closure devices described above can also include alignment markings positioned on the exterior adjacent the distal end of the proximal housing. For example, vessel closure devices 110 can also include one or more alignment marks, such as alignment marks 200a, 200b and 200c, as illustrated in FIG. 13. Alignment marks 200 provide a visual reference relative to the relative orientation of needles 138. In this particular embodiment, needles 138a and 138b are aligned with alignment mark 200a, such that when device 110 is rotated and oriented so that alignment mark 200a is positioned directly on top of handle 118 (i.e., vertically oriented), then the relative position of needles 138a and 138b would also be substantially vertically oriented relative to the axis 128 of shaft 112. Thus, when device 110 is rotated clockwise until alignment mark 200b is vertically oriented (i.e., is positioned at the twelve o'clock), then the relative position of needles 138a and 138b would be oriented at an approximately 60 degree angle relative to the vertical (oriented in the clockwise direction). Conversely, when device 110 is rotated counter-clockwise until alignment mark 200c is vertically oriented (i.e., is positioned at the twelve o'clock), then the relative position of needles 138a and 138b would be oriented at an approximately 60 degree angle relative to the vertical, but oriented in the counter-clockwise direction.

Figure 14C:
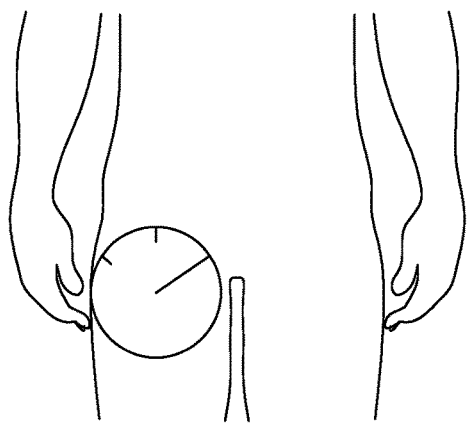

Thus, alignment marks 200 provide a visual guide to allow the surgeon to selectively and accurately locate one or more sutures across the vessel puncture at different angular orientations. In the case of multiple sutures, this would require a separate vessel closure device 110 for each suture. For example, if two sutures were desired at different angular positions, a first closure device 110 would be used to place a first suture across the vessel opening at a first angular orientation as graphically depicted in FIG. 14A. The first suture would be cut, but not tied, and then the first closure device is removed, leaving the guidewire in place. Then a second suture device 110 would be inserted over the guidewire and properly positioned within the same vessel opening. However, using one of the other the alignment marks, the second device would be positioned at a different angular orientation to place the second suture across the vessel opening at a second angular orientation (as graphically illustrated in FIG. 14B). Once the second device is removed, then both the first and second sutures could be tied, closing off the vessel puncture site. And, as indicated in FIG. 14C, this process could be extended as needed to provide a third suture.

In operation, a tissue suturing device is used by advancing a needle distally to penetrate the tissue and position a suture through the tissue. In various embodiments described herein, attaching the suture to the needle is accomplished by moving the needles distally through a housing of a device to connect to the suture. The suture is positioned through the tissue by withdrawing the needle proximally through the proximal end of the housing. Finally, the needle can be separated from the suture by drawing the suture across the suture cutting blade to sever the needle from the suture.

The various embodiments of a suturing device described herein can be provided to position a suture across an opening in a wall of a blood vessel to close the opening. In a femoral artery closure procedure, for example, such devices are used to advance the suture and the needle percutaneously through subcutaneous tissue to a blood vessel access site.

The present invention offers surgeons an automated method for delivering a pre-tied knot to an incision formed in a tissue wall. The present invention simplifies the effort associated with a surgeon manually delivering a knot to an incision site. Thus, the present invention reduces the time required to accurately and precisely place a suture knot in close proximity to an incision formed in a lumen, thereby decreasing both the overall time a patient spends in procedure and recovery and the costs associated therewith.

While the exemplary embodiments have been described in some detail for clarity of understanding, a wide variety of modifications, adaptations, and changes will be apparent to those of skill in the art. Hence, the scope of the present invention is limited solely by the appended claims.

What is claimed is:

1. An improved actuation and control mechanism intended for use in a vessel closure device for closing an opening or puncture in a vessel wall having an elongate shaft having a longitudinal axis, a housing positioned at the proximal end of the shaft, a flexible, atraumatic monorail guidebody positioned at the distal end of the shaft, a foot articulatably mounted proximate the distal end of the shaft, the foot being movable between a first, parked position, in which the foot is substantially aligned along the axis of the shaft, and a second, deployed position, in which the foot extends laterally away from the shaft, the foot having a first and a second end, the first end and the second end each having a needle receptacle with a cuff positioned therein, a length of suture located within the foot and extending between the cuffs, and a pair of needles located within the shaft that can be selectively advanced through the vessel wall adjacent to the opening and into the cuffs located in the needle receptacles in the first and second ends of the foot, and that can be selectively withdrawn thereby drawing the suture through the vessel wall adjacent to the opening, the improved actuation and control mechanism for the vessel closure device comprising:
    a foot actuation handle operatively coupled to the foot, the foot actuation handle being selectively moveable linearly along the axis of the device between a distal position whereby the foot is positioned in its first, parked position, and a proximal position whereby the foot is positioned in its second, deployed position, the foot actuation handle comprising a pair of handles that extend laterally from opposing sides of the housing, and wherein the foot actuation handle is configured to be grasped and manipulated by a pair of fingers of one hand of a user; and
    a needle actuation handle operatively coupled to the needles, the needle actuation handle being selectively movably linearly along the axis of the device between a proximal position wherein the needles are located within the shaft and a distal position wherein the needles are advanced to engage the cuffs, and wherein the needle actuation handle is configured to be engaged and selectively manipulated by a thumb of the same one hand of the user.

2. The vessel closure device of claim 1, wherein the foot is deployed by axial movement of the foot actuation handle in the proximal direction relative to the needle actuation handle.

3. The vessel closure device of claim 2, wherein, once the foot is deployed by proximal movement of the foot actuation handle, the needles are deployed into engagement with the foot by axial movement of the needle actuation handle in the distal direction relative to the foot actuation handle.

4. The vessel closure device of claim 1 further comprising a first interlock mechanism that prevents the needle actuation handle from being advanced from its proximal position when the foot is positioned in its first, parked position, but allows the needle actuation handle to be advanced from its proximal position to its distal position after the foot is moved to its second, deployed position.

5. The vessel closure device of claim 4, wherein the first interlock mechanism comprises:
    a ball formed on a distal end of the needle actuation handle; and
    a pair of projections formed on the housing and engaging opposing sides of the ball to constrain movement of the ball until a predetermined amount of pressure is applied to the needle actuation handle force the ball past the projection.

6. The vessel closure device of claim 5, wherein projections are flexible and resilient and are configured bend upon application of the predetermined amount of pressure applied to the needle actuation handle to allow movement of the ball in the distal direction.

7. The vessel closure device of claim 5, wherein projections are configured break upon application of the predetermined amount of pressure applied to the needle actuation handle to allow movement of the ball in the distal direction.

8. The vessel closure device of claim 1 further comprising a second interlock mechanism that temporarily locks the foot actuation handle into place when it is moved from its distal position to its proximal position.

9. The vessel closure device of claim 8 wherein the second interlock mechanism automatically releases the foot actuation handle from its proximal position after the needle actuation handle is returned to its proximal position from its distal position.

10. The vessel closure device of claim 9 further comprising a return bias spring associated with the foot actuation handle for biasing the foot actuation handle toward its distal position.

11. The vessel closure device of claim 10, wherein the second interlock mechanism comprises:
    a pair of lock detents positioned on an inner surface of the foot actuation handle;
    a pair of lock windows formed in opposing sides of the housing and positioned so as to receive the lock detents when the foot actuation handle is moved to its proximal position and thereby temporarily lock the foot actuation handle in its proximal position; and a pair of flanges formed on an inner portion of the needle actuation handle, the flanges being configured to engage the lock detents and release the lock detents from the lock windows as the needle actuation handle is withdrawn from its distal position to its proximal position.

12. The vessel closure device of claim 1 further comprising one or more alignment marks positioned on an exterior surface of a distal end of the housing, each alignment mark being located at a pre-selected rotational position relative to the needles.

13. The vessel closure device of claim 12, wherein a first one of the one or more alignment marks is vertically aligned with the needles.

14. The vessel closure device of claim 13, wherein a second one of the one or more alignment marks is located at an angle of about 60 degrees in a clockwise direction relative to the first one of the one or more alignment marks.

15. The vessel closure device of claim 14, wherein a third one of the one or more alignment marks is located at an angle of about 60 degrees in a counter-clockwise direction relative to the first one of the one or more alignment marks.

* * * * *